(12) United States Patent
Yamaguchi et al.

(10) Patent No.: US 10,981,865 B2
(45) Date of Patent: Apr. 20, 2021

(54) SUBSTITUTED OR UNSUBSTITUTED ALLYL GROUP-CONTAINING MALEIMIDE COMPOUND, PRODUCTION METHOD THEREFOR, AND COMPOSITION AND CURED PRODUCT USING SAID COMPOUND

(71) Applicant: DIC Corporation, Tokyo (JP)

(72) Inventors: Junji Yamaguchi, Tokyo (JP); Tomohiro Shimono, Ichihara (JP); Kazuo Arita, Sakura (JP); Masato Otsu, Sakura (JP)

(73) Assignee: DIC Corporation, Tokyo (JP)

( * ) Notice: Subject to any disclaimer, the term of this patent is extended or adjusted under 35 U.S.C. 154(b) by 234 days.

(21) Appl. No.: 16/304,875

(22) PCT Filed: Jun. 1, 2017

(86) PCT No.: PCT/JP2017/020418
§ 371 (c)(1),
(2) Date: Nov. 27, 2018

(87) PCT Pub. No.: WO2017/209236
PCT Pub. Date: Dec. 7, 2017

(65) Prior Publication Data
US 2020/0325101 A1    Oct. 15, 2020

(30) Foreign Application Priority Data

Jun. 3, 2016  (JP) .............................. JP2016-111865

(51) Int. Cl.
| C07D 207/452 | (2006.01) |
| B32B 15/08 | (2006.01) |
| B32B 27/34 | (2006.01) |
| C08F 22/40 | (2006.01) |
| C08G 59/50 | (2006.01) |
| C08J 5/24 | (2006.01) |
| H01L 23/29 | (2006.01) |
| H01L 23/31 | (2006.01) |

(52) U.S. Cl.
CPC .......... C07D 207/452 (2013.01); B32B 15/08 (2013.01); B32B 27/34 (2013.01); C08F 22/40 (2013.01); C08G 59/5053 (2013.01); C08J 5/24 (2013.01); H01L 23/295 (2013.01); H01L 23/31 (2013.01)

(58) Field of Classification Search
CPC ... C07D 207/452; H01L 23/295; H01L 23/31; B32B 15/08; B32B 27/34; C08G 59/5053; C08F 22/40; C08J 5/24
See application file for complete search history.

(56) References Cited

U.S. PATENT DOCUMENTS

| 3,931,224 | A |  | 1/1976 | Santa et al. |  |
| 4,168,366 | A |  | 9/1979 | D'Alelio |  |
| 4,808,646 | A | * | 2/1989 | Dahms | C07D 207/452 428/473.5 |
| 4,861,650 | A | * | 8/1989 | Dahms | C07D 207/452 442/179 |
| 4,924,005 | A | * | 5/1990 | Dahms | C07D 207/452 548/521 |
| 5,159,030 | A |  | 10/1992 | Hefner, Jr. |  |
| 5,364,700 | A | * | 11/1994 | Domeier | C08F 22/40 428/367 |
| 5,760,165 | A |  | 6/1998 | Dao et al. |  |
| 7,704,624 | B2 | * | 4/2010 | Jiang | H01M 8/0228 429/437 |
| 7,786,225 | B2 | * | 8/2010 | Yasumura | H01M 8/106 525/530 |

(Continued)

FOREIGN PATENT DOCUMENTS

| CN | 105153009 A | 12/2015 |
| JP | 2003-226691 A | 8/2003 |
| JP | 2011-173827 A | 9/2011 |
| JP | 2015-193628 A | 11/2015 |
| WO | 03/035407 A1 | 5/2003 |
| WO | 03/074516 A1 | 9/2003 |
| WO | 2016-052290 A1 | 4/2016 |

OTHER PUBLICATIONS

Haoyu Tang et al., "Synthesis, preparation and properties of novel high-performance allyl-maleimide resins," Polymer, 50, 2009, pp. 1414-1422. (cited in the ISR).

(Continued)

*Primary Examiner* — John P. Dulka
(74) *Attorney, Agent, or Firm* — Locke Lord LLP; James E. Armstrong, IV; Nicholas J. DiCeglie, Jr.

(57) ABSTRACT

Bismaleimides (BMI) exhibit excellent heat resistance (high Tg and high resistance to thermal decomposition) compared to epoxy resins and phenolic resins, and therefore, in recent years, more attention is paid to bismaleimides as a resin material for the next-generation devices represented by SiC power semiconductors, in addition to the investigation on the use of bismaleimides for electronic material applications. As such, conventional BMI's are known as highly heat-resistant resins; however, there is a demand for a resin having higher heat resistance for advanced material applications and the like. Thus, an object of the invention is to provide a novel maleimide compound having superior heat resistance. Disclosed is a substituted or unsubstituted allyl group-containing maleimide compound having a structure with three or more benzene rings, having one or more groups each having a substituted or unsubstituted allyl group, and having one or more maleimide groups.

19 Claims, No Drawings

(56) References Cited

U.S. PATENT DOCUMENTS

| | | | | |
|---|---|---|---|---|
| 8,497,953 | B2* | 7/2013 | Miyamoto | G02B 6/0051 349/64 |
| 9,217,053 | B2* | 12/2015 | Suzuki | H01L 23/293 |
| 9,374,895 | B2* | 6/2016 | Murakawa | H05K 1/092 |
| 9,676,959 | B2* | 6/2017 | Kuwana | C09K 19/00 |
| 9,690,013 | B2* | 6/2017 | Tajiri | C08L 67/00 |
| 9,708,535 | B2* | 7/2017 | Hasebe | C09K 19/56 |
| 9,939,555 | B2* | 4/2018 | Schadt | C08F 22/40 |
| 9,957,402 | B2* | 5/2018 | Miyamoto | B41J 2/01 |
| 9,994,772 | B2* | 6/2018 | Kuriyama | C09K 19/3003 |
| 10,059,798 | B2* | 8/2018 | Arita | C08G 63/00 |
| 10,113,028 | B2* | 10/2018 | Hirota | H05K 1/0366 |
| 10,113,096 | B2* | 10/2018 | Yuan | C08K 3/22 |
| 10,202,470 | B2* | 2/2019 | Endo | C08F 220/24 |
| 10,301,515 | B2* | 5/2019 | Matsumoto | C09J 7/385 |
| 10,399,312 | B2* | 9/2019 | Otsu | C08L 39/00 |
| 10,414,850 | B2* | 9/2019 | Imada | C08G 8/20 |
| 10,473,820 | B2* | 11/2019 | Yamamoto | C08F 22/20 |
| 10,539,714 | B2* | 1/2020 | Ishii | H01L 51/004 |
| 10,788,715 | B2* | 9/2020 | Kinoshita | G02F 1/133711 |
| 2015/0118499 | A1* | 4/2015 | Suzuki | C08G 16/0243 428/418 |
| 2015/0344617 | A1* | 12/2015 | Arita | C08G 63/137 428/209 |
| 2016/0130391 | A1* | 5/2016 | Arita | H05K 1/0326 525/449 |
| 2018/0199435 | A1* | 7/2018 | Ohnishi | C08F 220/18 |
| 2018/0362480 | A1* | 12/2018 | Arita | H01L 23/31 |
| 2019/0119489 | A1* | 4/2019 | Nakatani | C08G 73/124 |
| 2019/0144372 | A1* | 5/2019 | Arita | C07C 215/78 528/367 |
| 2020/0109276 | A1* | 4/2020 | Otsu | C08J 5/24 |
| 2020/0325100 | A1* | 10/2020 | Yamaguchi | C08L 35/00 |

OTHER PUBLICATIONS

Elango Kumarasamy et al., "Tailoring Atropisomeric Maleimides for Stereospecific [2+2] Photocycloaddition-Photochemical and Photophysical Investigations Leading to Visible-Light Photocatalysis," Journal of the American Chemical Society, 136, 2014, pp. 8729-8737. (cited in the ISR).

Jin Wen Bin et al., "Structure-Activity Relationship Study of Permethyl Ningalin B Analogues as P-Glycoprotein Chemosensitizers," Journal of Medicinal Chemistry, 2013, 56, pp. 9057-9070. (cited in the ISR).

Chia-Fu Cheng et al., "Total synthesis of (+−)-camphorataimides and (+−)-himanimides by NaBH4/Ni(OAc)2 or Zn/AcOH stereoselective reduction," Tetrahedron, 2008, vol. 64, 4347-4353.(cited in the ISR).

International Search Report dated Jul. 11, 2017, issued for PCT/JP2017/020418.

H. Tang et al., "Synthesis, preparation and properties of novel high-performance allyl-maleimide resins", Polymer, vol. 50, No. 6, 2009, pp. 1414-1422. (cited in the Oct. 15, 2019 Search Report issued for EP17806786.4).

T. Tamamura: "Soluble and Curable Prepolymers from Polyallyl Ester Monomers Containing Aromatic Imide Groups", Journal of Polymer Science, Polymer Chemistry Edition., vol. 17, 1979, pp. 2351-2361. (cited in the Oct. 15, 2019 Search Report issued for EP17806786.4).

S. K. Dolui et al., "Heat Resistant Allylic Resin Matrix for Composite", European Polymer Journal, vol. 22, No. 5, 1986, pp. 361-368. (cited in the Oct. 15, 2019 Search Report issued for EP17806786.4).

G. Li et al., "Synthesis and in-vitro biological activity of macrocyclic urea Chk1 inhibitors", Bioorganic & Medicinal Chemistry Letters, vol. 17, 2007, pp. 6499-6504. (cited in the Oct. 15, 2019 Search Report issued for EP17806786.4).

B. A. Tagiev, "New Method for Synthesis of Aromatic Diimide Dicarboxylic Acid Diallyl Esters", Russian Journal of Applied Chemistry, vol. 84, No. 3, 2011, pp. 412-415. (cited in the Oct. 15, 2019 Search Report issued for EP17806786.4).

Supplementary European Search Report dated Oct. 15, 2019, issued for the European patent application No. 17806786.4.

Communication issued in corresponding European Patent Application No. 17806786.4, dated Aug. 3, 2020 (and its Japanese translation).

J. W. Bin et al. "Structure-Activity Relationship Study of Permethyl Ningalin B Analogues as P-Glycoprotein Chemosensitizers," Journal of Medicinal Chemistry, 9057-9070, (2013).

C-F Cheng et al., "Total synthesis (±)-camphorataimides and (±)-himanimides by NaBH4/Ni(OAc)2 or Zn/AcOH stereoselective reduction," Tetrahedron 64, 4347-4353, (2008).

E. Kumarasamy et al., "Tailoring Atropisomeric Maleimides for Stereospecific [2+2] Photocycloaddition-Photochemical and Photophysical Investigations Leading to Visible-Light Photocatalysis," Journal of the American Chemical Society 136, 8729-8737, (2014).

Haoyu Tang, Wanwan Li, Xinghe Fan, Xiaofang Chen, Zhihao Shen and Qifeng Zhou; Synthesis, preparation and properties of novel high-performance allyl-maleimide resins; Polymer, vol. 50, Issue 6, Mar. 6, 2009, pp. 1414-1422.

* cited by examiner

SUBSTITUTED OR UNSUBSTITUTED ALLYL GROUP-CONTAINING MALEIMIDE COMPOUND, PRODUCTION METHOD THEREFOR, AND COMPOSITION AND CURED PRODUCT USING SAID COMPOUND

CROSS REFERENCE TO RELATED APPLICATIONS

This application is related to co-pending application: "SUBSTITUTED OR UNSUBSTITUTED ALLYL GROUP-CONTAINING MALEIMIDE COMPOUND, PRODUCTION METHOD THEREFOR, AND COMPOSITION AND CURED PRODUCT USING SAID COMPOUND" filed even date herewith in the names of Junji YAMAGUCHI, Tomohiro SHIMONO, Kazuo ARITA and Masato OTSU as a national phase entry of PCT/JP2017/020419, which application is assigned to the assignee of the present application and is incorporated by reference herein.

TECHNICAL FIELD

The present invention relates to a substituted or unsubstituted allyl group-containing maleimide compound, a method for production thereof, and a composition and a cured product produced using the compound.

BACKGROUND ART

As circuit board materials for electronic equipment, prepregs obtainable by impregnating glass clothes with thermosetting resins such as an epoxy resin, a benzoxazine resin, and a BT (bismaleimide-triazine) resin, heating and drying the impregnated glass clothes; laminated plates obtained by heating and curing the prepregs; and multilayer plates obtained by combining the laminated plates and the prepregs and heating and curing the combinations, are widely used.

In recent years, in regard to these various use applications, particularly advanced material applications, there is a demand for materials and compositions that have further enhanced performances, which are represented by heat resistance, dielectric characteristics, and moisture resistance reliability, and have these performances in combination, and that exhibit superior flame retardancy as well.

Above all, bismaleimides (BMI) exhibit excellent heat resistance (high Tg and high resistance to thermal decomposition) compared to conventional epoxy resins and phenolic resins, and therefore, in recent years, more attention is paid to bismaleimides as a resin material for the next-generation devices represented by SiC power semiconductors, in addition to the investigation on the use of bismaleimides for the above-mentioned electronic material applications. For example, in the market, BMI's having DDM (4,4'-diaminodiphenylmethane) and DDE (4,4'-diaminodiphenyl ether) skeletons have been distributed as highly heat-resistant resins.

CITATION LIST

Patent Literature

Patent Literature 1: JP-A-2015-193628

SUMMARY OF INVENTION

Technical Problem

As described above, BMI's are conventionally known as highly heat-resistant resins; however, there is a demand for a resin having superior heat resistance for advanced material applications and the like.

Thus, it is an object of the present invention to provide a novel maleimide compound having superior heat resistance.

Solution to Problem

The inventors of the present invention conducted a thorough investigation, and as a result, the inventors found that the problem described above can be solved by a substituted or unsubstituted allyl group-containing maleimide compound having a structure with three or more benzene rings and having one or more substituted or unsubstituted allyl groups as well as one or more maleimide groups.

That is, this invention relates to a substituted or unsubstituted allyl group-containing maleimide compound, which is a compound having a structure with three or more benzene rings, having one or more groups each having a substituted or unsubstituted allyl group, and having one or more maleimide groups.

Advantageous Effects of Invention

According to the invention, a substituted or unsubstituted allyl group-containing maleimide compound having superior heat resistance is provided. Thereby, the substituted or unsubstituted allyl group-containing maleimide compound can be suitably used for use applications such as heat-resistant members and electronic members, particularly a semiconductor encapsulating material, a circuit board, a buildup film, a buildup substrate, an adhesive, a resist material, a matrix resin for a fiber-reinforced resin, a highly heat-resistant prepreg, and a resin for a heat-resistant coating material.

DESCRIPTION OF EMBODIMENTS

<Substituted or Unsubstituted Allyl Group-Containing Maleimide Compound>

The substituted or unsubstituted allyl group-containing maleimide compound of the invention has a structure with three or more benzene rings, has one or more groups each having a substituted or unsubstituted allyl group, and has one or more maleimide groups.

When the substituted or unsubstituted allyl group-containing maleimide compound has the above-described configuration, superior heat resistance can be realized compared to conventional maleimide compounds. Particularly, when the substituted or unsubstituted allyl group-containing maleimide compound has three or more benzene rings, the thermal decomposition resistance temperature can be increased.

Furthermore, according to an embodiment, the substituted or unsubstituted allyl group-containing maleimide compound may have a low melting point.

Since conventional maleimide compounds have high melting points and do not melt at low temperatures, these maleimide compounds have poor handleability. Furthermore, for example, even if conventional maleimide compounds are incorporated into curable resins, since compatibility is markedly poor, various components react and cure locally, and therefore, uniform cured products cannot be produced. This has been one of the factors limiting the use applications of maleimide compounds.

In contrast, since the substituted or unsubstituted allyl group-containing maleimide compound has a low melting point, the compound has high handleability. Furthermore, for example, the maleimide compound has excellent compatibility with a curable resin in a curable resin, and a uniform composition can be produced. Thus, it is possible to produce a cured product suitably.

Incidentally, the reason why the substituted or unsubstituted allyl group-containing maleimide compound has excellent solvent solubility is not necessarily clearly understood; however, it is speculated to be because the substituted or unsubstituted allyl group in the structure alleviates the crystallinity originating from aromatic ring.

Furthermore, according to an embodiment, the substituted or unsubstituted allyl group-containing maleimide compound also has excellent solvent solubility.

Conventional maleimide compounds have low solvent solubility and cannot be used in the form of using a solvent in combination, such as a coating liquid. This has been one of the factors limiting the use applications of the maleimide compounds.

In contrast, since the substituted or unsubstituted allyl group-containing maleimide compound has excellent solvent solubility, the maleimide compound can also be used in the form of a coating liquid or the like. Thereby, the maleimide compound can be suitably applied to use applications such as a resin for a heat-resistant coating material, to which conventional maleimide compounds cannot be applied.

Incidentally, the reason why the substituted or unsubstituted allyl group-containing maleimide compound has excellent solvent solubility is not necessarily clearly understood; however, it is speculated to be because the affinity for solvents is increased due to the presence of a substituted or unsubstituted allyl group in the structure.

The substituted or unsubstituted allyl group-containing maleimide compound of the invention has a structure with three or more benzene rings. At this time, the benzene rings may or may not have a substituent, and the mode of bonding is not particularly limited. The benzene rings may be linked directly to one another or may be linked through linking groups, or it is still acceptable that the benzene rings are fused with one another and form a fused ring.

Preferred examples of the structure having three or more benzene rings include structures of the following Formulae (1-1) to (1-11).

[Chem. 1]

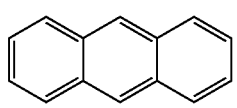
(1-1)

(1-2)

-continued

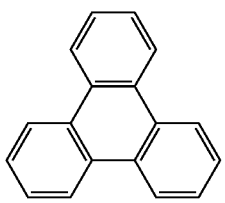
(1-3)

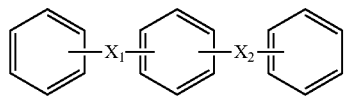
(1-4)

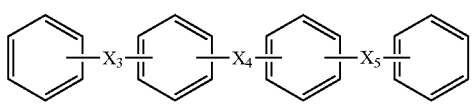
(1-5)

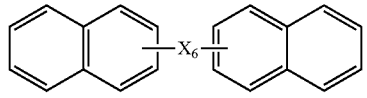
(1-6)

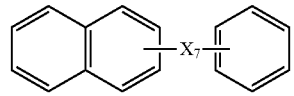
(1-7)

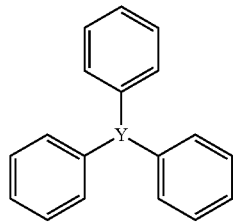
(1-8)

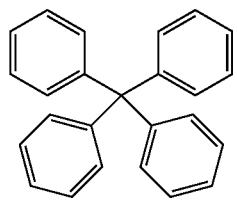
(1-9)

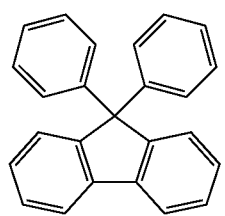 [SMILES: c1ccc(C2(c3ccccc3)c3ccccc3-c3ccccc32)cc1]
(1-10)

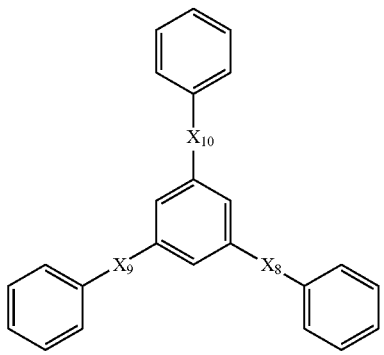

(1-11)

In Formulae (1-1) to (1-11), the benzene rings may each have a substituent.

In this regard, examples of the substituent for the benzene rings include, but are not limited to, an alkyl group having 1 to 10 carbon atoms, an alkenyl group having 2 to 10 carbon atoms, an alkynyl group having 2 to 10 carbon atoms, an aryl group having 6 to 10 carbon atoms, an alkoxy group having 1 to 10 carbon atoms, an alkylcarbonyl group having 2 to 10 carbon atoms, an alkyloxycarbonyl group having 2 to 10 carbon atoms, an alkylcarbonyloxy group having 2 to 10 carbon atoms, a halogen atom, a hydroxyl group, an amino group, an amide group, a ureido group, a urethane group, a carboxyl group, a thioether group, a cyano group, and a nitro group.

Examples of the alkyl group having 1 to 10 carbon atoms include, but are not limited to, a methyl group, an ethyl group, a propyl group, an isopropyl group, a cyclopropyl group, a butyl group, an isobutyl group, a sec-butyl group, a tert-butyl group, a cyclobutyl group, a pentyl group, a 2-methylbutyl group, a 3-methylbutyl group, a hexyl group, a cyclohexyl group, a nonyl group, and a decyl group.

Examples of the alkenyl group having 2 to 10 carbon atoms include, but are not limited to, a vinyl group, an allyl group, a propenyl group, an isopropenyl group, a 1-butenyl group, a 2-butenyl group, a 3-butenyl group, a 1-hexenyl group, a 2-hexenyl group, a 3-hexenyl group, a 4-hexenyl group, and a 5-hexenyl group.

Examples of the alkynyl group having 2 to 10 carbon atoms include, but are not limited to, an ethynyl group, a propynyl group, a 1-butynyl group, a 2-butynyl group, a 3-butynyl group, a 1-hexynyl group, a 2-hexynyl group, a 3-hexynyl group, a 4-hexynyl group, and a 5-hexynyl group.

Examples of the aryl group having 6 to 10 carbon atoms include, but are not limited to, a phenyl group and a naphthyl group.

Examples of the alkoxy group having 1 to 10 carbon atoms include, but are not limited to, a methoxy group, an ethoxy group, a propyloxy group, an isopropyloxy group, a butoxy group, a pentyloxy group, a hexyloxy group, and a cyclohexyloxy group.

Examples of the alkylcarbonyl group having 2 to 10 carbon atoms include, but are not limited to, a methylcarbonyl group, an ethylcarbonyl group, a propylcarbonyl group, an isopropylcarbonyl group, a butylcarbonyl group, a pentylcarbonyl group, a hexylcarbonyl group, a cyclohexylcarbonyl group, and a nonylcarbonyl group.

Examples of the alkyloxycarbonyl group having 2 to 10 carbon atoms include, but are not limited to, a methyloxycarbonyl group, an ethyloxycarbonyl group, a propyloxycarbonyl group, a butyloxycarbonyl group, a hexyloxycarbonyl group, and a cyclohexyloxycarbonyl group.

Examples of the alkylcarbonyloxy group having 2 to 10 carbon atoms include, but are not limited to, a methylcarbonyloxy group, an ethylcarbonyloxy group, a propylcarbonyloxy group, a butylcarbonyloxy group, a hexylcarbonyloxy group, and a cyclohexylcarbonyloxy group.

Examples of the halogen atom include a fluorine atom, a chlorine atom, a bromine atom, and an iodine atom.

Incidentally, each of the benzene rings may have the above-mentioned substituents singly or in combination of two or more kinds thereof.

$X_1$ to $X_{10}$ described above each independently represent a direct bond, a hydrocarbon group having 1 to 3 carbon atoms which may have a substituent, an oxygen atom, a sulfur atom, or a sulfonyl group. Incidentally, usually, $X_1$ to $X_{10}$ are each a divalent linking group.

Examples of the hydrocarbon group having 1 to 3 carbon atoms include methylene, ethylene, and propylene.

In this case, examples of the substituent for the hydrocarbon group include an alkyl group having 1 to 5 carbon atoms, such as a methyl group, an ethyl group, a propyl group, or a butyl group; and a halogenated alkyl group having 1 to 5 carbon atoms, such as a fluoromethyl group, a difluoromethyl group, a trifluoromethyl group, a chloromethyl group, a dichloromethyl group, a trichloromethyl group, a bromomethyl group, a dibromomethyl group, a tribromomethyl group, a chlorofluoromethyl group, or a pentafluoroethyl group.

In the description given above, $X_1$ to $X_{10}$ are each preferably a direct bond, a hydrocarbon group having one carbon atom, an oxygen atom, or a sulfur atom.

Y described above represents a carbon atom which may have a substituent, or a nitrogen atom. At this time, examples of the substituent that can be carried by the carbon atom are the same as the examples of the substituent of the hydrocarbon group as described above. Incidentally, usually, Y is a trivalent or tetravalent linking group, and preferably a trivalent linking group.

Among the above-mentioned structures having three or more benzene rings, structures of Formulae (1-4), (1-5), (1-8), (1-9), (1-10), and (1-11) are preferred; structures of Formulae (1-5), (1-8), and (1-10) are more preferred; structures of the following Formulae (1-5-1), (1-5-2), (1-8-1), and (1-8-2) are even more preferred; and structures of the following Formulae (1-8-1) and (1-8-2) are particularly preferred.

[Chem. 2]

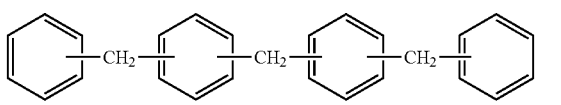

(1-5-1)

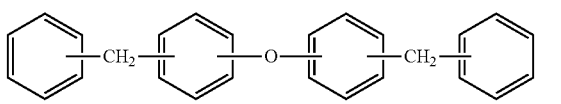

(1-5-2)

(1-8-1)

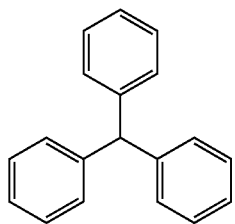

(1-8-2)

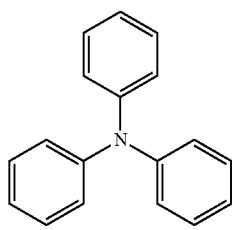

Incidentally, in Formulae (1-5-1), (1-5-2), (1-8-1), and (1-8-2), the benzene rings may each have a substituent. At this time, examples of the substituent are the same as the examples of the above-mentioned substituent of the benzene ring.

The substituted or unsubstituted allyl group-containing maleimide compound of the invention may have only one of the structures represented by Formulae (1-1) to (1-11), or may have two or more thereof. According to an embodiment, it is preferable that the substituted or unsubstituted allyl group-containing maleimide compound has three to five benzene rings, and more preferably three to four benzene rings, in the structure. When the number of benzene rings in the structure is 3 or larger, the maleimide compound has excellent heat resistance, which is preferable. Meanwhile, when the number of benzene rings in the structure is 5 or less, the molecular structure becomes compact, and therefore, the melting point is not too high, while the maleimide compound has excellent handleability, which is preferable.

Preferred examples of the structure having three or more benzene rings include structures represented by the following formulae.

[Chem. 3]

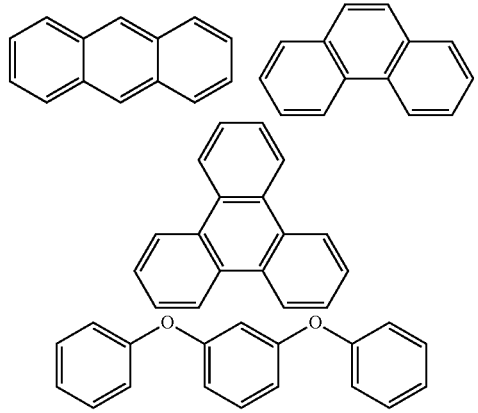

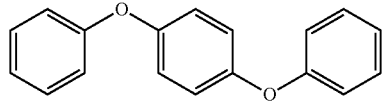

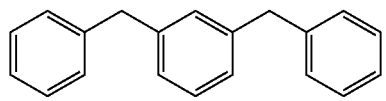

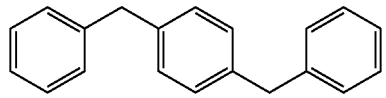

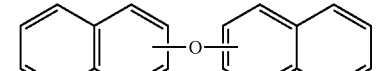

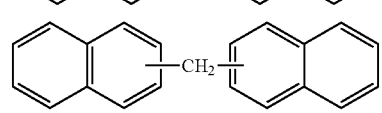

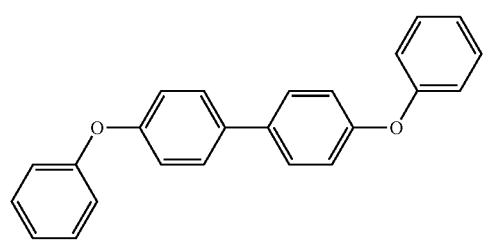

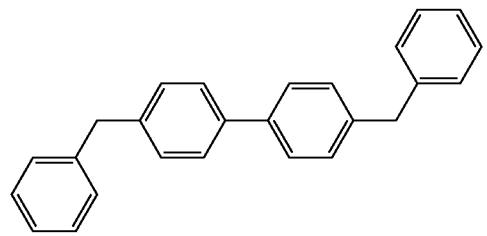

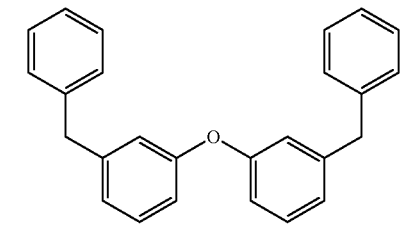

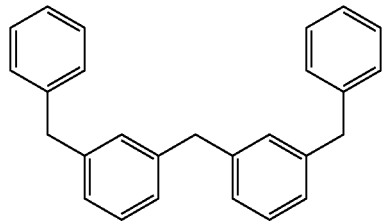

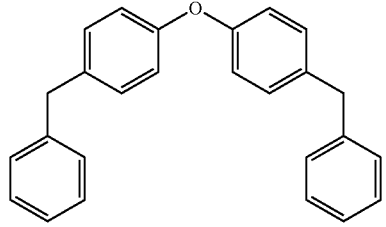

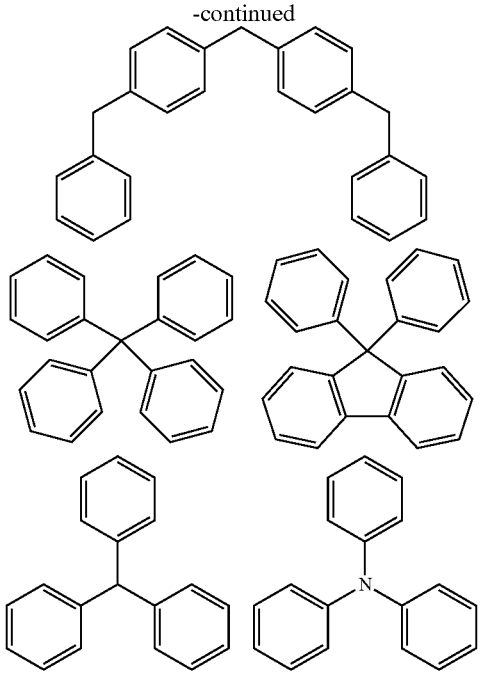

Incidentally, the structure having three or more benzene rings may have a substituent to the extent that the effects of the invention are not impaired. Examples of the substituent include the above-mentioned examples of the substituent of the benzene ring. At this time, the benzene rings may have the substituents singly or in combination of two or more kinds thereof.

In the description given above, more preferred examples of the structure having three or more benzene rings include structures represented by the following formulae.

[Chem. 4]

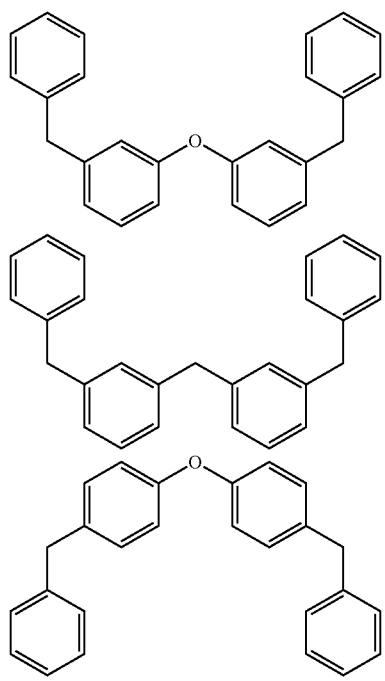

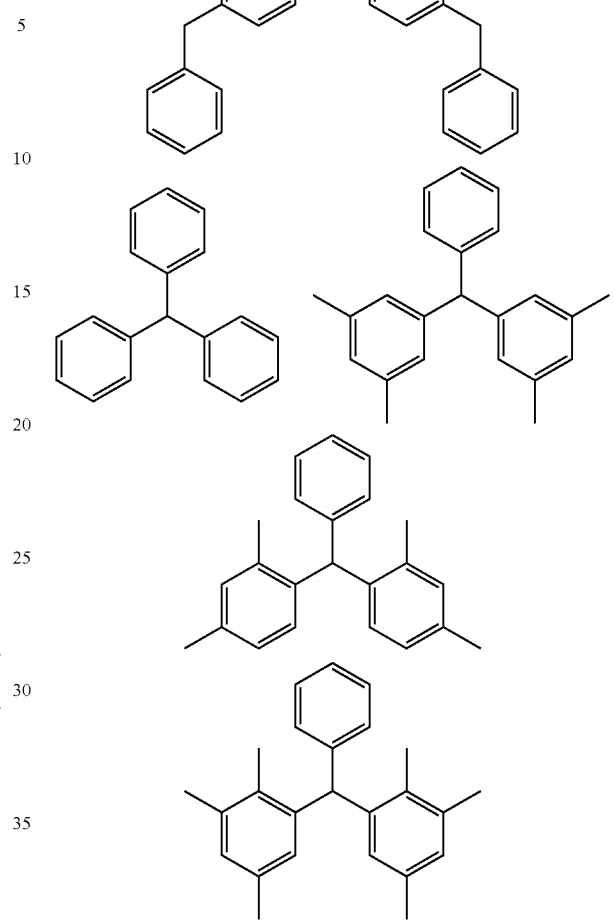

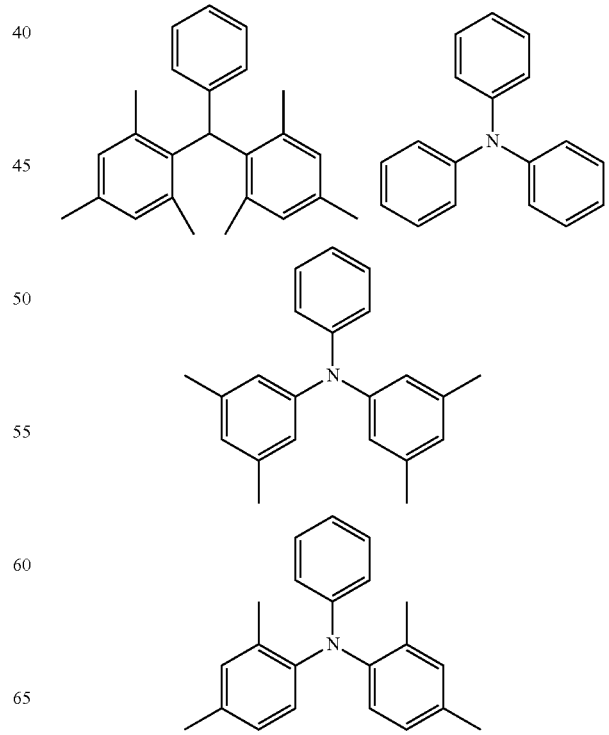

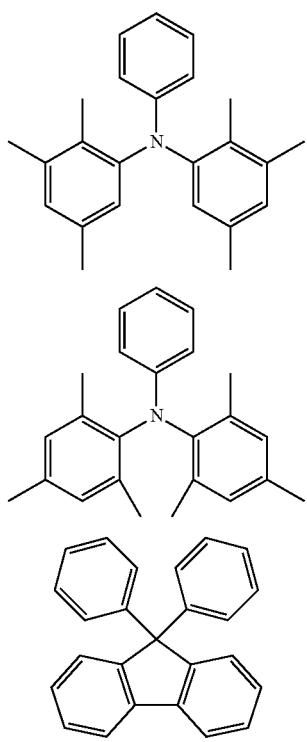

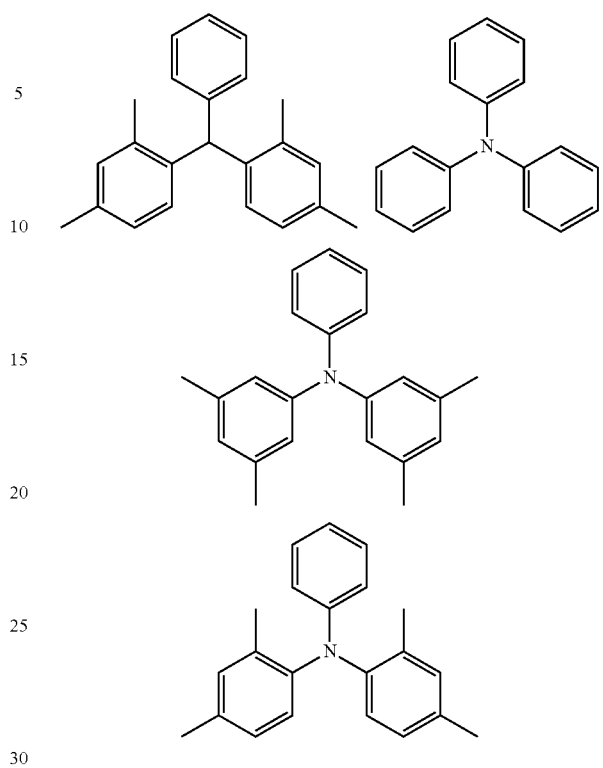

In the description given above, even more preferred examples of the structure having three or more benzene rings include structures represented by the following formulae.

[Chem. 5]

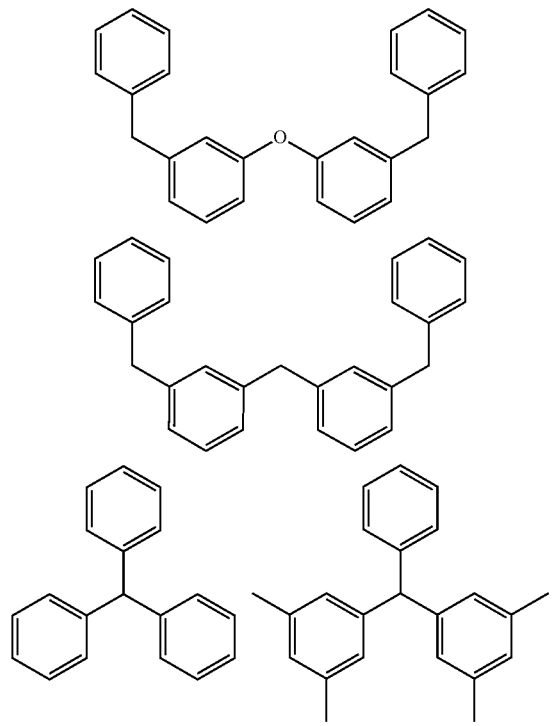

In the description given above, particularly preferred examples of the structure having three or more benzene rings include structures represented by the following formulae.

[Chem. 6]

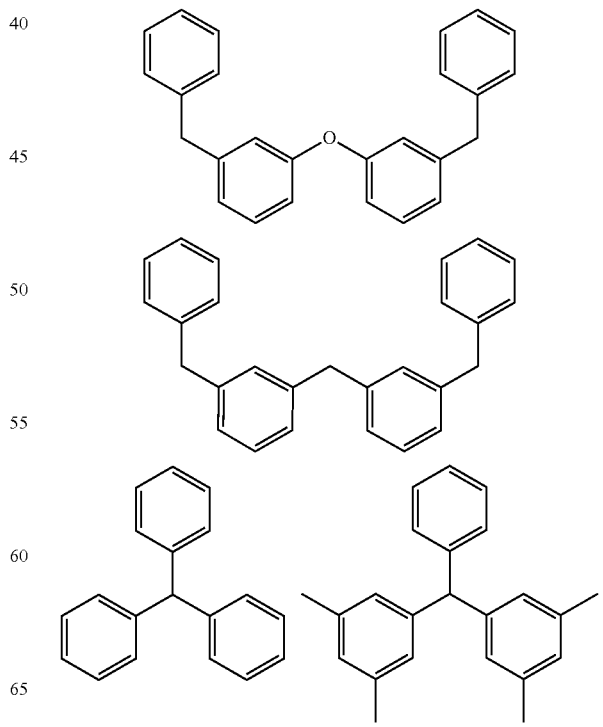

-continued

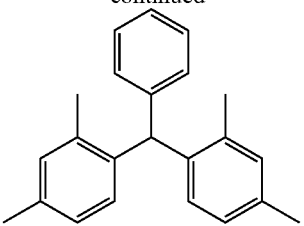

Furthermore, the substituted or unsubstituted allyl group-containing maleimide compound of the invention has one or more groups each having a substituted or unsubstituted allyl group and further has one or more maleimide groups. Incidentally, according to the present specification, the term "substituted or unsubstituted allyl group" means an allyl group, or a group in which at least one of hydrogen atoms bonded to the carbon atoms constituting a double bond of an allyl group has been substituted by a methyl group. Specifically, examples of the substituted or unsubstituted allyl group include groups represented by the following structural formulae.

[Chem. 7]

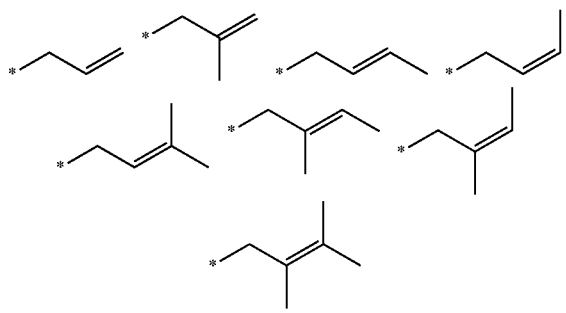

Incidentally, in the formulae described above, the symbol "*" represents a site that is bonded to another group. Among these, examples of the substituted or unsubstituted allyl group preferably include groups represented by structural formulae.

[Chem. 8]

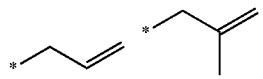

The group having a substituted or unsubstituted allyl group and the maleimide group are usually bonded directly to benzene rings in the structure having three or more benzene rings.

According to an embodiment, there are no particular limitations on the places of bonding of the group containing a substituted or unsubstituted allyl group and the maleimide group; however, it is preferable that the maleimide group and the group containing a substituted or unsubstituted allyl group exist on the same benzene ring, because heat resistance is further enhanced.

Furthermore, according to an embodiment, the numbers of the groups containing a substituted or unsubstituted allyl group and the maleimide groups are preferably such that there are two groups containing a substituted or unsubstituted allyl group and one maleimide group; one group containing a substituted or unsubstituted allyl group and two maleimide groups; or two groups containing a substituted or unsubstituted allyl group and two maleimide groups. It is more preferable that there are two groups containing a substituted or unsubstituted allyl group and one maleimide group; or two groups containing a substituted or unsubstituted allyl group and two maleimide groups. It is even more preferable that there are two groups containing a substituted or unsubstituted allyl group and two maleimide groups.

According to an embodiment, the substituted or unsubstituted allyl group-containing maleimide compound is preferably represented by the following Formula (2).

[Chem. 9]

$$[\text{Aly}\!\!-\!\!]_n\text{A}\!\!-\!\![\text{MI}]_m \quad (2)$$

In Formula (2), n and m each independently represent an integer from 1 to 5, more preferably 1 to 4, even more preferably 1 or 2, and particularly preferably 2.

The ratio of m and n is such that m:n=1:5 to 5:1, preferably 1:2 to 2:1, and more preferably 1:1. Incidentally, when the ratio m:n is in the above-described range, it is particularly preferable because a balance between heat resistance and low melting point can be achieved.

Aly represents a group containing a substituted or unsubstituted allyl group represented by the following Formula (3).

[Chem. 10]

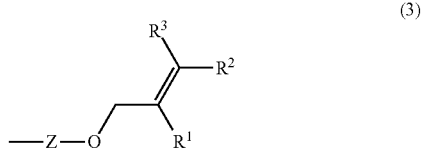

In Formula (3), Z represents a direct bond, or a hydrocarbon group having 1 to 10 carbon atoms which may have a substituent; and $R^1$, $R^2$, and $R^3$ each independently represent a hydrogen atom or a methyl group.

Examples of the hydrocarbon group having 1 to 10 carbon atoms include an alkylene group, an alkenylene group, an alkynylene group, a cycloalkylene group, an arylene group, and groups combining a plurality of those.

Examples of the alkylene group include a methylene group, a methyne group, an ethylene group, a propylene group, a butylene group, a pentylene group, and a hexylene group.

Examples of the alkenylene group include a vinylene group, a 1-methylvinylene group, a propenylene group, a butenylene group, and a pentenylene group.

Examples of the alkynylene group include an ethynylene group, a propynylene group, a butynylene group, a pentynylene group, and a hexynylene group.

Examples of the cycloalkylene group include a cyclopropylene group, a cyclobutylene group, a cyclopentylene group, and a cyclohexylene group.

Examples of the arylene group include a phenylene group, a tolylene group, a xylylene group, and a naphthylene group.

Among these, Z is preferably a direct bond or methylene, and more preferably a direct bond.

Specific examples of the structure of Aly include the following structural formulae.

[Chem. 11]

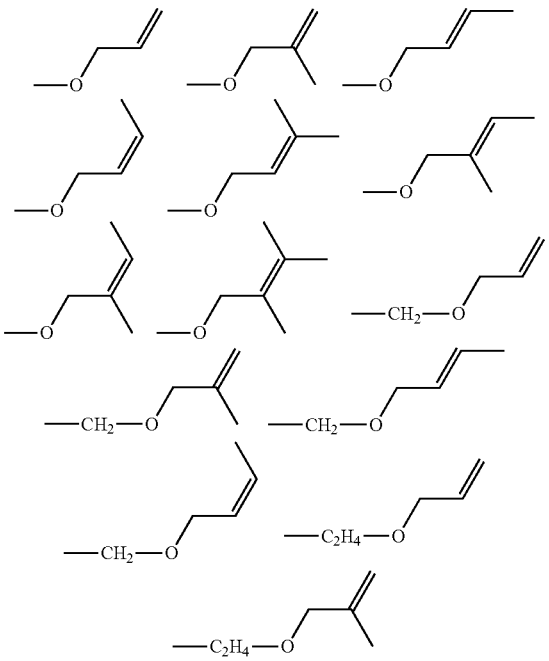

Among these, it is preferable that Aly is represented by any one of the following structural formulae.

[Chem. 12]

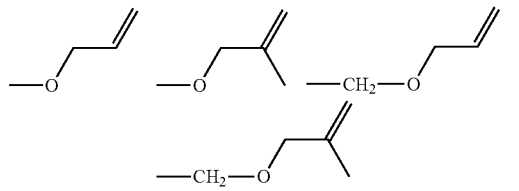

Furthermore, MI represents a maleimide group represented by the following Formula (4).

[Chem. 13]

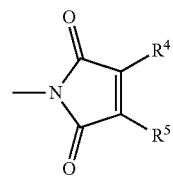

(4)

In Formula (4), $R^4$ and $R^5$ each independently represent a hydrogen atom or a methyl group.

According to an embodiment, there are no particular limitations on the places of bonding of the group containing a substituted or unsubstituted allyl group and the maleimide group; however, it is preferable that the maleimide group and the group containing a substituted or unsubstituted allyl group exist on the same benzene ring, because heat resistance is further enhanced.

Furthermore, A represents a structure having three or more benzene rings. At this time, the structure having three or more benzene rings is similar to the structure described above.

Preferred examples of the structure of the allyl group-containing maleimide compound of the invention include structures represented by the following Formulae (5-1) to (5-33).

[Chem. 14]

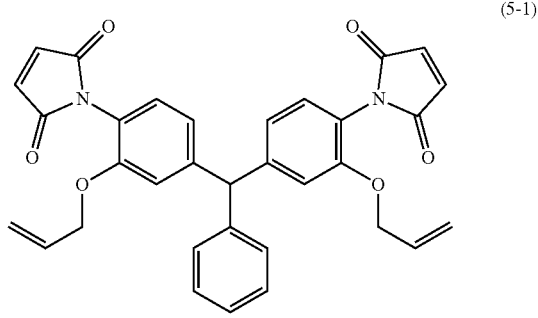

(5-1)

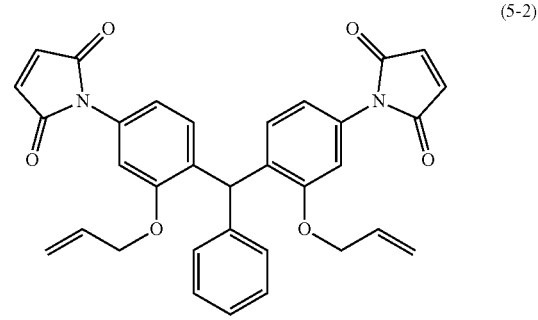

(5-2)

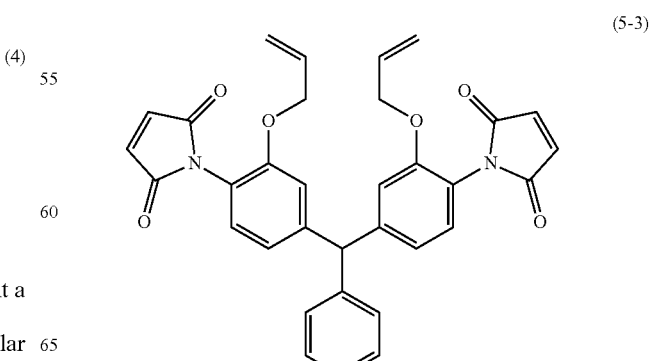

(5-3)

-continued
(5-4)
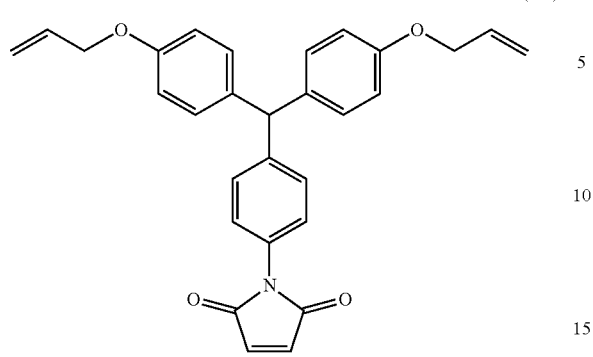
(5-5)
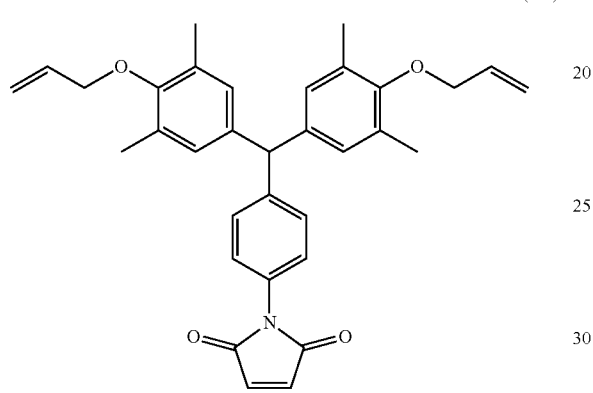
(5-6)
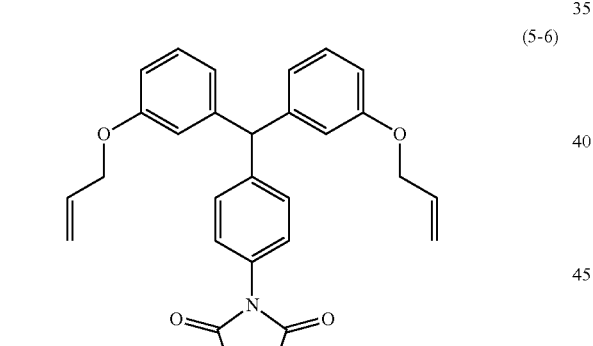
(5-7)
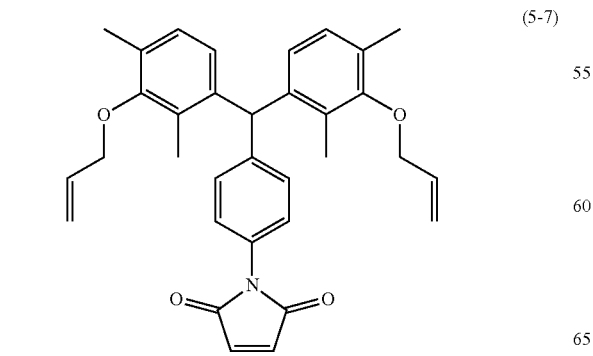
-continued
(5-8)
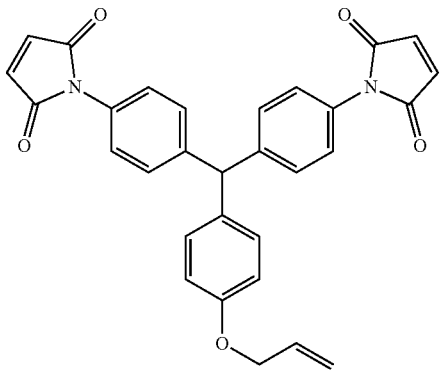
(5-9)
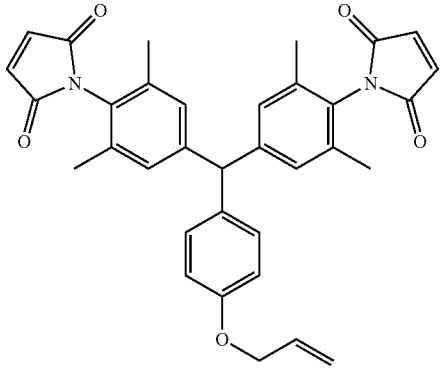
(5-10)
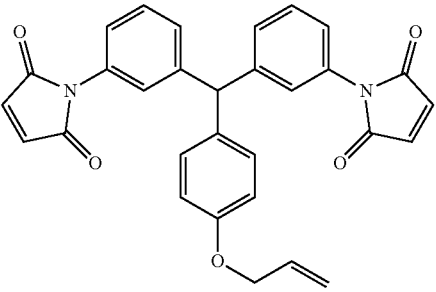
(5-11)
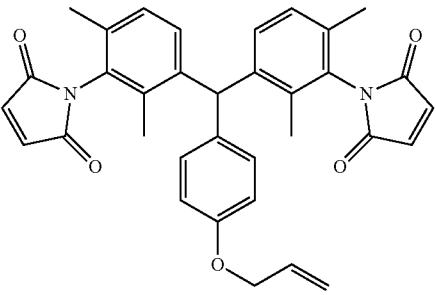
(5-12)
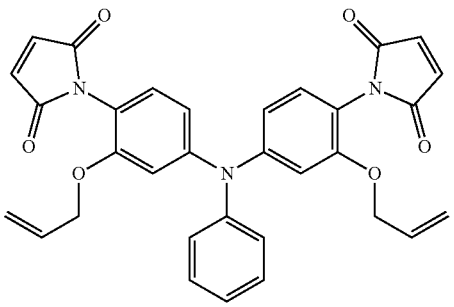

-continued
(5-13)
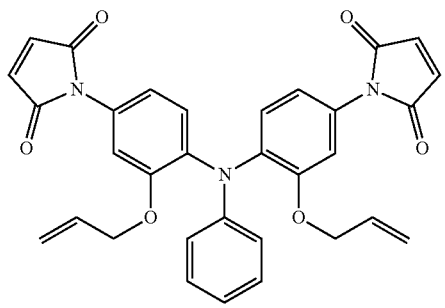
(5-14)
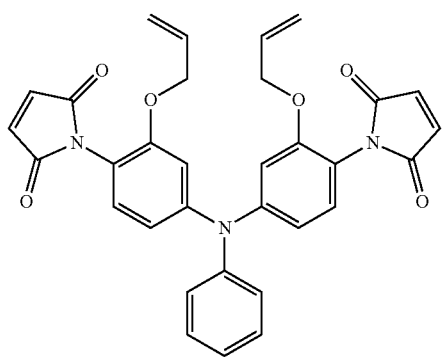
(5-15)
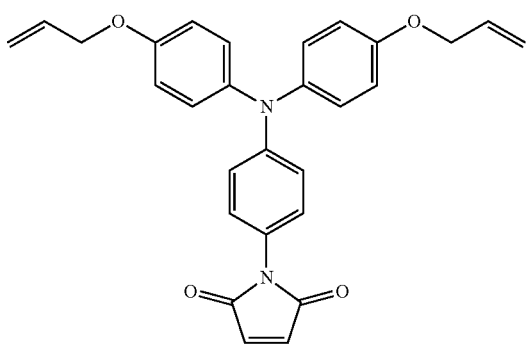
[Chem. 15]
(5-16)
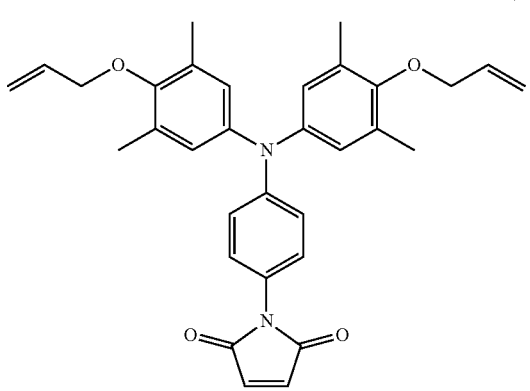
-continued
(5-17)
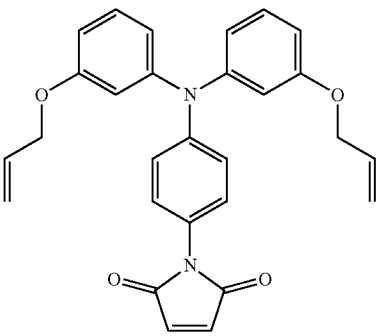
(5-18)
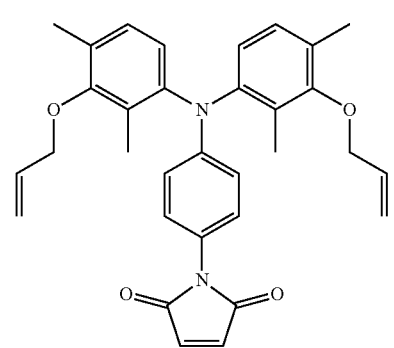
(5-19)
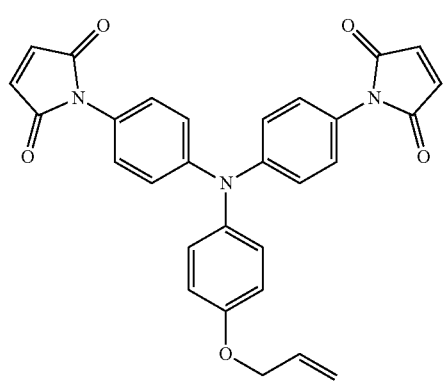
(5-20)
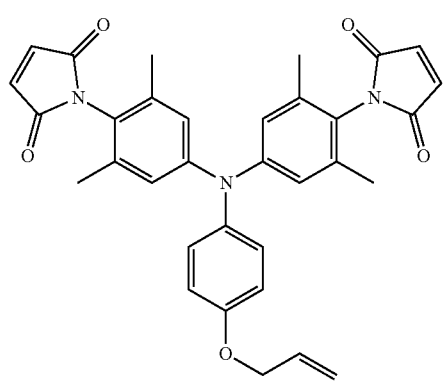

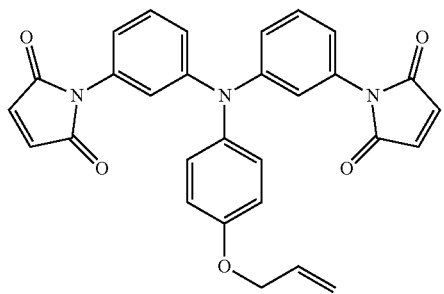
(5-21)
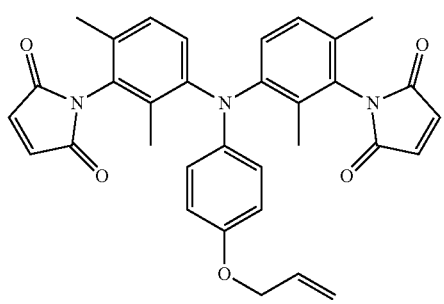
(5-22)
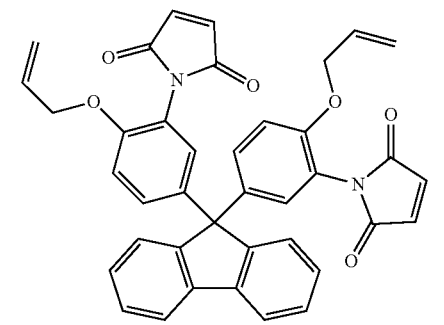
(5-23)
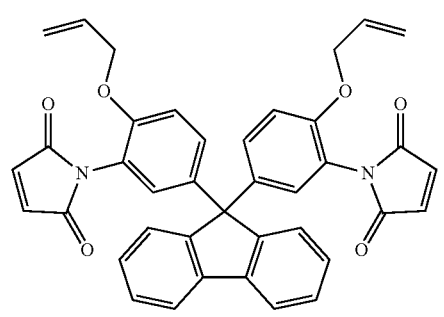
(5-24)
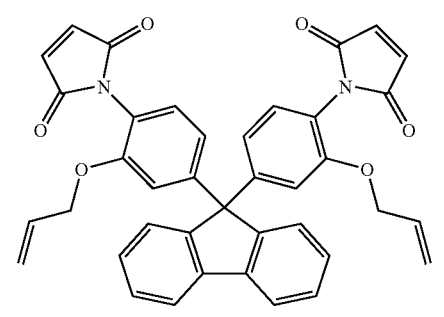
(5-25)
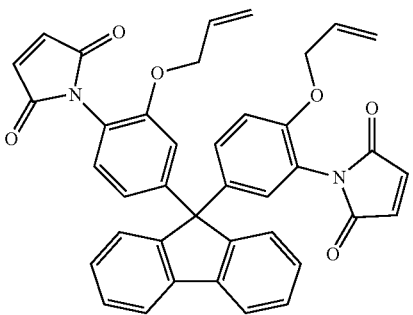
(5-26)
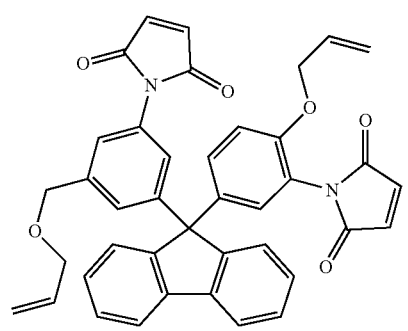
(5-27)
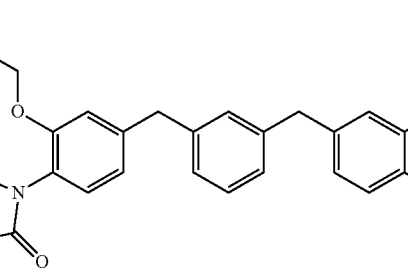
(5-28)
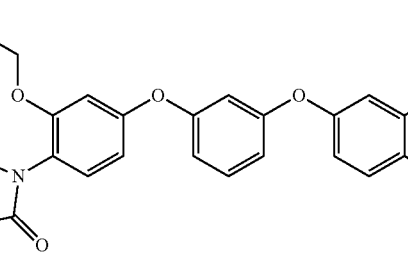
(5-29)
[Chem. 16]
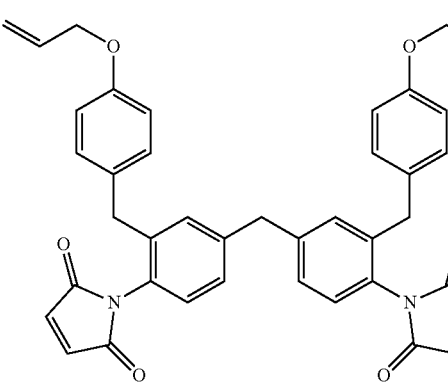
(5-30)

-continued (5-31)
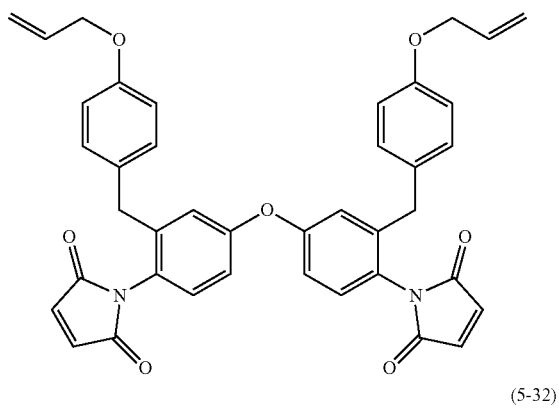

(5-32)
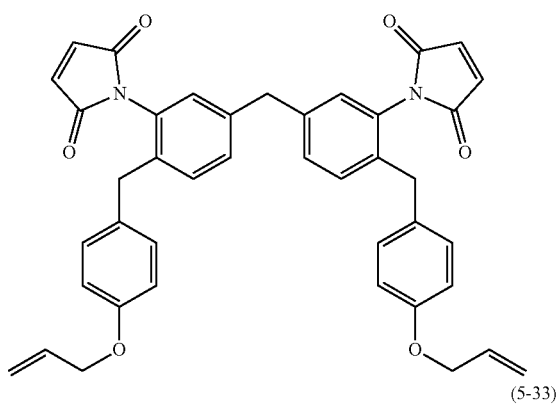

(5-33)
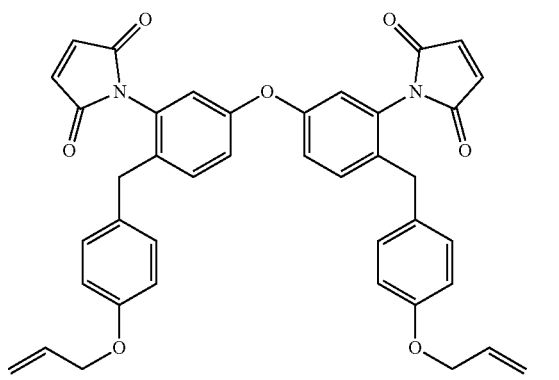

Among these, structures represented by Formulae (5-1) to (5-22) and (5-30) to (5-33) are preferred; structures represented by Formulae (5-1) to (5-7), (5-12) to (5-18), and (5-30) to (5-33) are more preferred; structures represented by Formulae (5-1), (5-3) to (5-5), (5-12), (5-13), (5-15), (5-16), and (5-30) to (5-33) are even more preferred; structures represented by Formulae (5-1), (5-3), (5-12), (5-14), and (5-30) to (5-33) are particularly preferred; and structures represented by Formulae (5-1), (5-3), (5-12), and (5-14) are most preferred.

<Method for Producing Substituted or Unsubstituted Allyl Group-Containing Maleimide Compound>

The method for producing a substituted or unsubstituted allyl group-containing maleimide compound of the invention is not particularly limited; however, production can be carried out efficiently by implementing the following steps:

1-1) a step of protecting an amino group of a hydroxyl group-containing aromatic amino compound having three or more benzene rings 1-2) a step of introducing a substituted or unsubstituted allyl group into a hydroxyl group of the compound obtained in step 1-1)

1-3) a step of deprotecting the protected amino group of the compound obtained in step 1-2)

1-4) a step of maleimidating an amino group of the compound obtained in step 1-3)

The substituted or unsubstituted allyl group-containing maleimide compound according to the invention can be efficiently produced by a production method including the above-described steps.

Here, by using a hydroxyl group-containing aromatic amino compound having three or more benzene rings in step (1-1), the substituted or unsubstituted allyl group-containing maleimide compound of the invention, which is a compound having a structure with three or more benzene rings, having one or more groups having a substituted or unsubstituted allyl group, and having one or more maleimide groups, can be produced.

The hydroxyl group-containing aromatic amino compound having three or more benzene rings is preferably a compound having the structure represented by Formula (1-1) or (1-2), a hydroxyl group, and an amino group. Specific examples include, but are not limited to, conventionally known compounds such as 9,9-bis(3-amino-4-hydroxyphenyl)fluorene, 1,3-bis(4-amino-3-hydroxyphenoxy)benzene, and 4,4'-diamino-4"-hydroxytriphenylamine.

Incidentally, examples of the method for producing the hydroxyl group-containing aromatic amino compound having three or more benzene rings include a method of nitrating a hydroxyl group-containing aromatic compound and then reducing the resultant; a method of reacting a hydroxyl group-containing aromatic compound with a nitro group-containing aromatic aldehyde and then reducing the reaction product; and a method of reacting an amino group-containing aromatic compound with a hydroxyl group-containing aromatic aldehyde. Furthermore, a method of reacting an amino group-containing aromatic compound with a methoxy group-containing aromatic aldehyde, or a method of reacting an amino group- and methoxy group-containing aromatic compound with an aromatic aldehyde, subsequently deprotecting a methoxy group, and converting the methoxy group into a hydroxyl group, may also be used.

Protection of an amino group in step 1-1) may be carried out using a conventionally known method, and for example, an amino group can be protected by acetylating the amino group. At this time, for the acetylation, any conventionally known acetylating agent may be used, and examples of the agent include acetic anhydride and acetyl chloride.

In regard to step 1-2), a substituted or unsubstituted allyl group can be introduced by, for example, reacting a hydroxyl group of a hydroxyl group-containing aromatic amino compound having a protected amino group with a halide of a substituted or unsubstituted allyl group-containing compound in the presence of a base. Examples of the halide of a substituted or unsubstituted allyl group-containing compound include allyl bromide, methallyl bromide (3-bromo-2-methyl-1-propene), allyl chloride, methallyl chloride (3-chloro-2-methyl-1-propene), cis-1-chloro-2-butene, trans-1-chloro-2-butene, 1-chloro-3-methyl-2-butene, and 1-bromo-3-methyl-2-butene. Furthermore, examples of the base include potassium carbonate.

In step 1-3) and step 1-4), the protected amino group is deprotected, and that amino group is maleimidated. Maleimidation of the amino group can be achieved by, for example, reacting the amino group with a compound represented by the following Formula (6).

[Chem. 17]

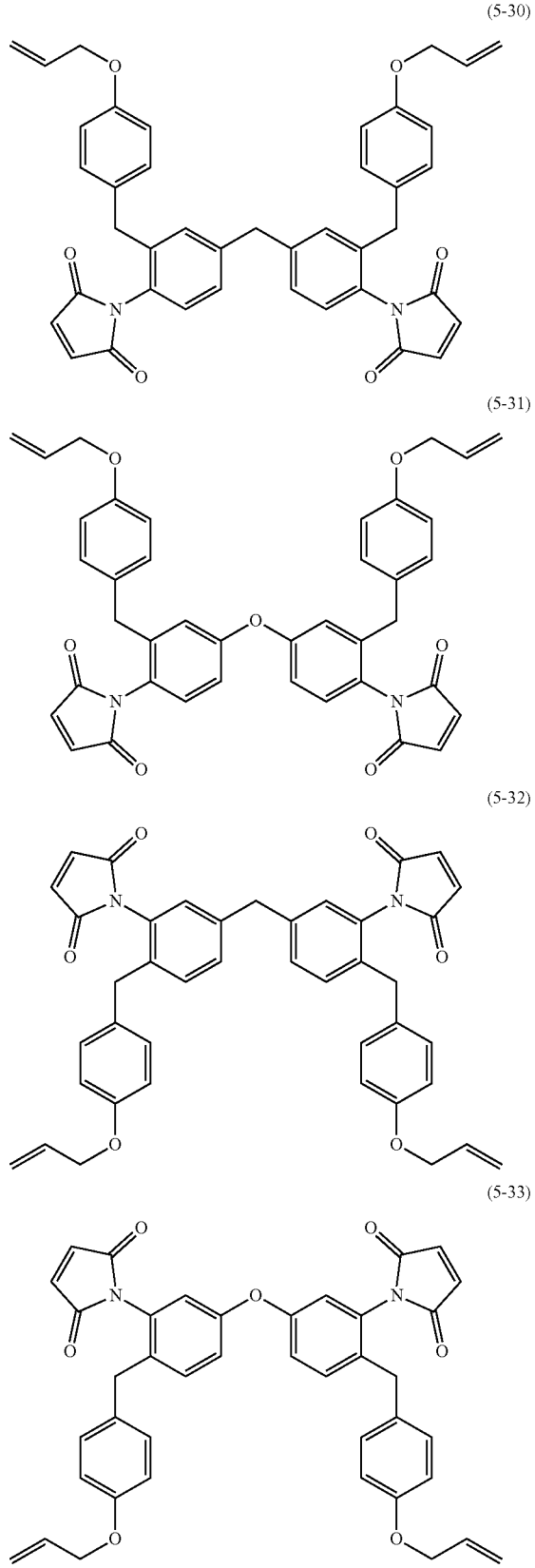

(5-30)
(5-31)
(5-32)
(5-33)

In Formula (6), $R^4$ and $R^5$ each independently represent a hydrogen atom or a methyl group.

Examples of the compound represented by Formula (6) include maleic anhydride, citraconic anhydride, and 2,3-dimethylmaleic anhydride.

When the above-described steps are carried out, the substituted or unsubstituted allyl group-containing maleimide compound of the invention, which is a compound having a structure with three or more benzene rings, having one or more groups each having a substituted or unsubstituted allyl group, and having one or more maleimide groups, can be produced.

In the case of synthesizing the substituted or unsubstituted allyl group-containing maleimide compound of the invention, unreacted monomers may remain in the reaction system, or other compounds that are different from the substituted or unsubstituted allyl group-containing maleimide compound may be produced as products. Examples of the other compounds include non-cyclized amic acid, isoimide, monomers, and an oligomer of a product. In regard to these substances other than the substituted or unsubstituted allyl group-containing maleimide compound, the substances may be eliminated by implementing purification processes, or depending on the use application, the maleimide compound may be used while having those substances incorporated therein.

<Composition>

The composition of the invention includes the substituted or unsubstituted allyl group-containing maleimide compound of the invention.

Since the substituted or unsubstituted allyl group-containing maleimide compound according to the invention has excellent heat resistance, a cured product obtainable by curing a composition including this compound has excellent resistance to thermal decomposition, has a high glass transition temperature, and undergoes low linear expansion, the cured product can be suitably used for heat-resistant members or electronic members.

Furthermore, as described above, according to an embodiment, the substituted or unsubstituted allyl group-containing maleimide compound has a low melting point and exhibits low melting viscosity. Therefore, according to a preferred embodiment, a composition including a substituted or unsubstituted allyl group-containing maleimide compound and a resin is provided. This composition can be suitably applied particularly to semiconductor encapsulating material applications and the like.

Furthermore, as described above, according to an embodiment, the substituted or unsubstituted allyl group-containing maleimide compound has solvent solubility, too. Therefore, according to a preferred embodiment, a composition including the substituted or unsubstituted allyl group-containing maleimide compound and a dispersing medium is provided. This composition can be suitably applied to heat-resistant coating material applications and the like.

<Reactive Compound>

The composition of the present invention may include a reactive compound as a compounding substance in addition to the substituted or unsubstituted allyl group-containing maleimide compound of the invention. By including this reactive compound, various features such as reactivity, heat resistance, and handleability can be imparted to a resin.

The reactive compound as used herein is a compound having a reactive group, and this compound may be a monomer, an oligomer, or a polymer.

The reactive group may be a functional group that does not react with the substituted or unsubstituted allyl group-containing maleimide compound of the invention or may be a functional group that reacts with the maleimide compound. However, in order to further enhance heat resistance, the reactive group is preferably a functional group that reacts with the substituted or unsubstituted allyl group-containing maleimide compound of the invention.

Examples of the functional group that reacts with the allyl group-containing maleimide compound of the invention include an epoxy group, a cyanato group, a maleimide group, a phenolic hydroxyl group, an oxazine ring, an amino group, and a group having a carbon-carbon double bond.

Examples of a compound having an epoxy group include an epoxy resin and a phenoxy resin.

Examples of a compound having a cyanato group include a cyanate ester resin.

Examples of a compound having a maleimide group include a maleimide resin and a bismaleimide resin.

Examples of a compound having a phenolic hydroxyl group include a phenol novolac resin, a cresol novolac resin, a dicyclopentadiene-modified phenolic resin, a phenol aralkyl resin, a naphthol aralkyl resin, and a biphenyl aralkyl resin.

Examples of a compound having an oxazine ring include benzoxazine obtainable by reacting a phenolic compound or an aromatic amino compound with formaldehyde. These phenolic compound and aromatic amino compound may have a reactive functional group in the structure.

Examples of a compound having an amino group include aromatic amino compounds such as DDM (4,4'-diaminodiphenylmethane), DDE (4,4'-diaminodiphenyl ether), 3,4'-diaminodiphenyl ether, 2,2-{bis4-(4-aminophenoxy)phenyl}propane, and 4,4'-bis(4-aminophenoxy)biphenyl.

Examples of a compound having a group having a carbon-carbon double bond include a maleimide compound, a vinylic compound, and a (meth)allylic compound. Incidentally, according to the present specification, unless particularly stated otherwise, when a compound is described simply as "maleimide compound", this means that the compound is a maleimide compound other than the substituted or unsubstituted allyl group-containing maleimide compound according to the invention. Similarly, unless particularly stated otherwise, when a compound is described simply as "(meth) allylic compound", this means that the compound is a (meth)allylic compound other than the substituted or unsubstituted allyl group-containing maleimide compound according to the invention.

The above-described reactive compounds may have only one kind of reactive group, or may have a plurality of kinds of reactive groups. The number of functional groups may also be one or a plurality. Furthermore, it is also acceptable to use a plurality of kinds of reactive compounds at the same time.

Preferred examples of the reactive compound include an epoxy resin, a phenoxy resin, a cyanate ester resin, a maleimide compound, a vinylic compound, and an aromatic amino compound.

Among them, particularly preferred examples include a maleimide compound, a cyanate ester resin, an epoxy resin, and an aromatic amino compound.

A maleimide compound acquires an increased crosslinking density as a result of a self-addition reaction between the substituted or unsubstituted allyl group-containing maleimide compound and maleimide groups, or an ene reaction between an allyl group and a maleimide group. As the result, heat resistance, and particularly the glass transition temperature, is enhanced.

Usually, in order to obtain a uniform cured product using a maleimide compound, curing conditions of high temperature and a long time period are required. Therefore, in many cases, a peroxide-based catalyst is used in combination for acceleration of the reaction. However, the substituted or unsubstituted allyl group-containing maleimide compound of the invention undergoes a curing reaction even in a case in which no catalyst is used, and thus a uniform cured product can be obtained. When peroxide-based catalysts are used, there are problems such as an increase in the viscosity of the composition, a decrease in the pot life, and deterioration of physical properties caused by a trace amount of peroxides remaining in the cured product. However, since the substituted or unsubstituted allyl group-containing maleimide compound of the invention does not need to use a peroxide-based curing agent, those problems can be solved.

A cured product obtained from a cyanate ester resin and the substituted or unsubstituted allyl group-containing maleimide compound of the invention exhibits excellent dielectric characteristics.

When an epoxy resin is used in combination with the substituted or unsubstituted allyl group-containing maleimide compound of the invention, toughness or adhesiveness to metal can be imparted to the cured product.

An aromatic amino compound acquires an increased crosslinking density as a result of a Michael addition reaction between an amino group and a maleimide group, and the thermal decomposition resistance temperature and the glass transition temperature are increased.

The epoxy resin is not particularly limited as long as the resin has epoxy groups, and examples include a bisphenol A type epoxy resin, a bisphenol F type epoxy resin, a bisphenol E type epoxy resin, a bisphenol S type epoxy resin, a bisphenol sulfide type epoxy resin, a phenylene ether type epoxy resin, a naphthylene ether type epoxy resin, a biphenyl type epoxy resin, a tetraethylbiphenyl type epoxy resin, a polyhydroxynaphthalene type epoxy resin, a phenol novolac type epoxy resin, a cresol novolac type epoxy resin, a triphenylmethane type epoxy resin, a tetraphenylethane type epoxy resin, a dicyclopentadiene-phenol addition reaction type epoxy resin, a phenol aralkyl type epoxy resin, a naphthol novolac type epoxy resin, a naphthol aralkyl type epoxy resin, a naphthol-phenol co-condensed novolac type epoxy resin, a naphthol-cresol co-condensed novolac type epoxy resin, a naphthylene ether type epoxy resin, an aromatic hydrocarbon formaldehyde resin-modified phenolic resin type epoxy resin, a biphenyl-modified novolac type epoxy resin, and an anthracene type epoxy resin. These may be used singly, or two or more kinds thereof may be used in combination.

A phenoxy resin is a high-molecular weight thermoplastic polyether resin based on diphenol and epihalohydrin such as epichlorohydrin, and a phenoxy resin having a weight average molecular weight of 20,000 to 100,000 is preferred. Regarding the structure of the phenoxy resin, for example, a phenoxy resin having one or more skeletons selected from a bisphenol A skeleton, a bisphenol F skeleton, a bisphenol S skeleton, a bisphenol acetophenone skeleton, a novolac skeleton, a biphenyl skeleton, a fluorene skeleton, a dicyclopentadiene skeleton, a norbornene skeleton, a naphthalene skeleton, an anthracene skeleton, an adamantine skeleton, a terpene skeleton, and a trimethylcyclohexane skeleton, may be used.

Examples of the cyanate ester resin include a bisphenol A type cyanate ester resin, a bisphenol F type cyanate ester resin, a bisphenol E type cyanate ester resin, a bisphenol S type cyanate ester resin, a biphenol sulfide type cyanate ester resin, a phenylene ether type cyanate ester resin, a naphthylene ether type cyanate ester resin, a biphenyl type cyanate ester resin, a tetramethyl biphenyl type cyanate ester resin, a polyhydroxynaphthalene type cyanate ester resin, a phenol novolac type cyanate ester resin, a cresol novolac type cyanate ester resin, a triphenylmethane type cyanate ester resin, a tetraphenylethane type cyanate ester resin, a dicyclopentadiene-phenol addition reaction type cyanate ester resin, a phenol aralkyl type cyanate ester resin, a naphthol novolac type cyanate ester resin, a naphthol aralkyl type cyanate ester resin, a naphthol-phenol co-condensed novolac type cyanate ester resin, a naphthol-cresol co-condensed novolac type cyanate ester resin, an aromatic hydrocarbon formaldehyde resin-modified phenolic resin type cyanate ester resin, a biphenyl-modified novolac type cyanate ester resin, and an anthracene type cyanate ester resin. These may be used singly, or two or more kinds thereof may be used in combination.

Among these cyanate ester resins, particularly from the viewpoint that a cured product having excellent heat resistance is obtained, it is preferable to use a bisphenol A type cyanate ester resin, a bisphenol F type cyanate ester resin, a bisphenol E type cyanate ester resin, a polyhydroxynaphthalene type cyanate ester resin, a naphthylene ether type cyanate ester resin, or a novolac type cyanate ester resin. From the viewpoint that a cured product having excellent dielectric characteristics is obtained, a dicyclopentadiene-phenol addition reaction type cyanate ester resin is preferred.

Regarding the maleimide compound, examples include various compounds represented by any of the following Structural Formulae (i) to (iii).

[Chem. 18]

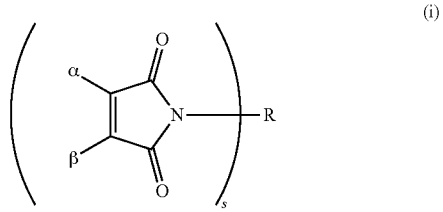

In Formula (i), R represents an s-valent organic group; α and β each represent any one of a hydrogen atom, a halogen atom, an alkyl group, and an aryl group; and s represent an integer of 1 or greater.

[Chem. 19]

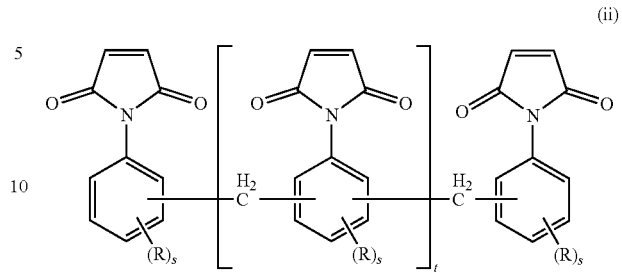

In Formula (ii), R represents any one of a hydrogen atom, an alkyl group, an aryl group, an aralkyl group, a halogen atom, a hydroxyl group, and an alkoxy group; s represents an integer from 1 to 3; and t represents the average number of the repeating units and is from 0 to 10.

[Chem. 20]

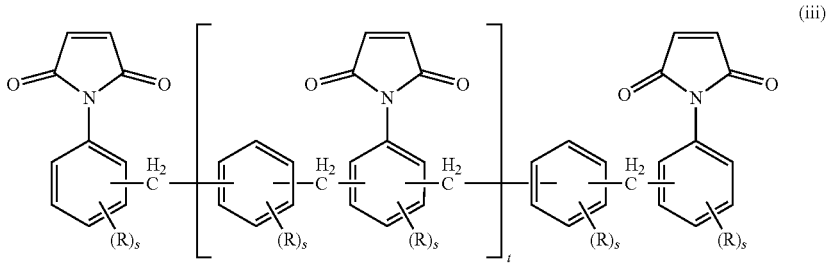

In Formula (iii), R represents any one of a hydrogen atom, an alkyl group, an aryl group, an aralkyl group, a halogen atom, a hydroxyl group, and an alkoxy group; s represents an integer from 1 to 3; and t represents the average number of the repeating units and is from 0 to 10.

These maleimide compounds may be used singly, or two or more kinds thereof may be used in combination.

Examples of the oxazine compound include, but are not limited to, a reaction product of bisphenol F, formalin, and aniline (F-a type benzoxazine resin); a reaction product of 4,4'-diaminodiphenylmethane, formalin, and phenol (P-d type benzoxazine resin); a reaction product of bisphenol A, formalin, and aniline; a reaction product of dihydroxydiphenyl ether, formalin, and aniline; a reaction product of diaminodiphenyl ether, formalin, and phenol; a reaction product of a dicyclopentadiene-phenol addition type resin, formalin, and aniline; a reaction product of phenolphthalein, formalin, and aniline; and a reaction product of dihydroxydiphenyl sulfide, formalin, and aniline. These may be used singly, or two or more kinds thereof may be used in combination.

Examples of the vinylic compound include alkyl (meth)acrylates having an alkyl group having 1 to 22 carbon atoms, such as methyl (meth)acrylate, ethyl (meth)acrylate, n-propyl (meth)acrylate, n-butyl (meth)acrylate, isobutyl (meth)acrylate, tert-butyl (meth)acrylate, 2-ethylhexyl (meth)acrylate, and lauryl (meth)acrylate; aralkyl (meth)acrylates such as benzyl (meth)acrylate and 2-phenylethyl (meth)acrylate; cycloalkyl (meth)acrylates such as cyclohexyl (meth)acrylate and isobornyl (meth)acrylate; ω-alkoxyalkyl (meth)acrylates such as 2-methoxyethyl (meth)acrylate and 4-methoxybutyl (meth)acrylate; carboxylic acid vinyl esters such as vinyl acetate, vinyl propionate, vinyl pivalate, and vinyl benzoate; alkyl esters of crotonic acid, such as methyl crotonate and ethyl crotonate; dialkyl esters of unsaturated dibasic acids, such as dimethyl malate, di-n-butyl malate, dimethylfumarate, and dimethyl itaconate; α-olefins such as ethylene and propylene; fluoroolefins such as vinylidene fluoride, tetrafluoroethylene, hexafluoropropylene, and chlorotrifluoroethylene; alkyl vinyl ethers such as ethyl vinyl ether and n-butyl vinyl ether; cycloalkyl vinyl ethers such as cyclopentyl vinyl ether and cyclohexyl vinyl ether; and tertiary amide group-containing monomers such as N,N-dimethyl(meth)acrylamide, N-(meth)acryloylmorpholine, N-(meth)acryloylpyrrolidine, and N-vinylpyrrolidone.

Examples of the (meth)allylic compound include allyl esters such as allyl acetate, allyl chloride, allyl caproate, allyl caprylate, allyl laurate, allyl palmitate, allyl stearate, allyl benzoate, allyl acetoacetate, and allyl lactate; allyloxy alcohols such as allyloxy methanol and allyloxy ethanol; compounds containing two allyl groups, such as diallyl phthalate, diallyl isophthalate, diallyl cyanurate, diallyl isocyanurate, pentaerythritol diallyl ether, trimethylolpropane diallyl ether, glycerin diallyl ether, bisphenol A diallyl ether, bisphenol F diallyl ether, ethylene glycol diallyl ether, diethylene glycol diallyl ether, triethylene glycol diallyl ether, propylene glycol diallyl ether, dipropylene glycol diallyl ether, and tripropylene glycol diallyl ether; compounds containing three or more allyl groups, such as triallyl isocyanurate, pentaerythritol triallyl ether, pentaerythritol tetraallyl ether, and trimethylolpropane triallyl ether; and methallyl forms of these compounds.

In the composition of the invention, a maleimide group and a substituted or unsubstituted allyl group both exist. The ratio of the maleimide group and the substituted or unsubstituted allyl group is not particularly limited; however, the ratio of the mole number of maleimide groups: mole number of substituted or unsubstituted allyl groups is preferably 1:10 to 10:1, and when the ratio is 1:5 to 5:1, it is preferable because heat resistance is excellent. Particularly, in the case of 1:2 to 2:1, it is preferable because the balance between heat resistance and the mixture viscosity is excellent. Incidentally, in a case in which a maleimide compound having a maleimide group, a (meth)allylic compound having a (meth)allyl group, and the like are included in the composition together with the substituted or unsubstituted allyl group-containing maleimide compound according to the invention, the "mole number of maleimide groups" and the "mole number of substituted or unsubstituted allyl groups" are calculated to include the mole numbers of the groups in compounds other than the substituted or unsubstituted allyl group-containing maleimide compound.

<Filler>

The composition of the invention may further include a filler, in addition to the substituted or unsubstituted allyl group-containing maleimide compound. Examples of the filler include inorganic fillers and organic fillers. Examples of the inorganic fillers include inorganic fine particles.

Examples of the inorganic fine particles include, as fine particles having excellent heat resistance, particles of alumina, magnesia, titania, zirconia, and silica (quartz, fumed silica, precipitated silica, silicic anhydride, fused silica, crystalline silica, ultrafine powder amorphous silica, and the like); as fine particles capable of excellent thermal conduction, particles of boron nitride, aluminum nitride, alumina oxide, titanium oxide, magnesium oxide, zinc oxide, silicon oxide, and diamond; as particles having excellent electrical conductivity, metal fillers and/or metal-coated fillers using simple metals or alloys (for example, iron, copper, magnesium, aluminum, gold, silver, platinum, zinc, manganese, and stainless steel); as fine particles having excellent barrier properties, particles of minerals such as mica, clay, kaolin, talc, zeolite, wollastonite, and smectite, and particles of potassium titanate, magnesium sulfate, sepiolite, zonolite, aluminum borate, calcium carbonate, titanium oxide, barium sulfate, zinc oxide, and magnesium hydroxide; as fine particles having high refractive indices, particles of barium titanate, zirconia oxide, and titanium oxide; as fine particles exhibiting photocatalytic properties, photocatalyst metals such as titanium, cerium, zinc, copper, aluminum, tin, indium, phosphorus, carbon, sulfur, tellurium, nickel, iron, cobalt, silver, molybdenum, strontium, chromium, barium, and lead, composites of the above-mentioned metals, and oxides of the metals and composites; as fine particles having excellent abrasion resistance, particles of metals such as silica, alumina, zirconia, and magnesium oxide, composites and oxides of those metals; as fine particles having excellent electrical conductivity, particles of metals such as silver and copper, tin oxide, and indium oxide; as fine particles having excellent insulating properties, particles of silica; and as fine particles having excellent ultraviolet shielding properties, particles of titanium oxide and zinc oxide.

These inorganic fine particles may be selected as appropriate depending on the use application, and the inorganic fine particles may be used singly or in combination of a plurality of kinds thereof. Furthermore, since the above-mentioned inorganic fine particles also have various characteristics in addition to the characteristics listed as examples, the inorganic fine particles may be selected as appropriately according to the use applications.

For example, in a case in which silica is used as the inorganic fine particles, known silica fine particles such as powdered silica or colloidal silica can be used without particular limitations. Examples of commercially available silica fine particles in a powder form include AEROSIL 50 and 200 manufactured by Nippon Aerosil Co., Ltd.; SHIELDEX H31, H32, H51, H52, H121, and H122 manufactured by AGC Inc.; E220A and E220 manufactured by Nippon Silica Industrial Co., Ltd.; SYLYSIA A470 manufactured by FUJI SILYSIA CHEMICAL, LTD.; and SG FLAKE manufactured by Nippon Sheet Glass Co., Ltd.

Furthermore, examples of commercially available colloidal silica include methanol silica sols, IPA-ST, MEK-ST, NBA-ST, XBA-ST, DMAC-ST, ST-UP, ST-OUP, ST-20, ST-40, ST-C, ST-N, ST-O, ST-50, and ST-OL, manufactured by Nissan Chemical Corporation.

Surface-modified silica fine particles may also be used, and examples thereof include a product obtained by surface-treating the above-described silica fine particles with a reactive silane coupling agent having a hydrophobic group, and a product obtained by modifying the silica fine particles with a compound having a (meth)acryloyl group. Examples of a commercially available powdered silica that has been modified with a compound having a (meth)acryloyl group include AEROSIL RM50 and R711 manufactured by Nippon Aerosil Co., Ltd., and examples of a commercially available colloidal silica that has been modified with a compound having a (meth)acryloyl group include MIBK-SD manufactured by Nissan Chemical Corporation.

The shape of the silica fine particles is not particularly limited, and particles having a spherical shape, a hollow shape, a porous shape, a rod shape, a sheet shape, a fibrous shape, or an undefined shape can be used. The primary particle size is preferably in the range of 5 to 200 nm. When the primary particle size is 5 nm or more, the inorganic fine particles are suitably dispersed in the dispersion, and when the primary particle size is 200 nm or less, a decrease in the strength of the cured product can be prevented.

Regarding titanium oxide fine particles, not only an extender pigment but also an ultraviolet light-responsive photocatalyst can be used, and for example, anatase type titanium oxide, rutile type titanium oxide, or brookite type titanium oxide can be used. Furthermore, particles designed to respond to visible light by doping a heteroelement into the crystal structure of titanium oxide can also be used. Regarding the element to be doped into titanium oxide, an anionic element such as nitrogen, sulfur, carbon, fluorine, or phosphorus; or a cationic element such as chromium, iron, cobalt, or manganese is suitably used. Regarding the form, a powder, a sol obtained by dispersing titanium oxide fine particles in an organic solvent or in water, or a slurry can be sued. Examples of commercially available titanium oxide fine particles in a powder form include AEROSIL P-25 manufactured by Nippon Aerosil Co., Ltd.; and ATM-100 manufactured by TAYCA CORPORATION. Furthermore, examples of commercially available titanium oxide fine particles in a slurry form include TKD-701 manufactured by TAYCA CORPORATION.

<Fibrous Substrate>

The composition of the invention may further include a fibrous substrate in addition to the substituted or unsubstituted allyl group-containing maleimide compound. The fibrous substrate of the invention is not particularly limited; however, a fibrous substrate that is used for fiber-reinforced resin is preferred, and inorganic fibers or organic fibers may be used.

Examples of the inorganic fibers include inorganic fibers such as carbon fibers, glass fibers, boron fibers, alumina fibers, and silicon carbide fibers; mineral fibers such as carbon fibers, activated carbon fibers, graphite fibers, glass fibers, tungsten carbide fibers, silicon carbide fibers, ceramic fibers, alumina fibers, natural fibers, and basalt; boron fibers, boron nitride fibers, boron carbide fibers, and metal fibers. Examples of the metal fibers include aluminum fibers, copper fibers, brass fibers, stainless steel fibers, and steel fibers.

Examples of the organic fibers include synthetic fibers formed from resin materials such as polybenzazole, aramid, polyparaphenylene benzoxazole (PBO), polyester, acrylics, polyamide, polyolefin, polyvinyl alcohol, and polyallylate; natural fibers formed from cellulose, pulp, cotton, wool, and silk; and regenerated fibers such as proteins, polypeptides, and alginate.

Among them, carbon fibers and glass fibers are preferable because their range of industrial utilization is wider. Among them, only one kind thereof may be used, or a plurality of kinds thereof may be used at the same time.

The fibrous substrate of the invention may be an aggregate of fibers, and the fibers may be in a continuous form or in a non-continuous form. The substrate may be a woven fabric or a non-woven fabric. Furthermore, the fibers may be in the form of a fiber bundle in which fibers are aligned in one direction, or may be in the form of a sheet in which fiber bundles are lined up. Furthermore, a three-dimensional shape obtained by providing a thickness to an aggregate of fibers may also be employed.

<Dispersing Medium>

The composition of the invention may also use a dispersing medium for the purpose of adjusting the solid content or viscosity of the composition. The dispersing medium may be a liquid medium that will not impair the effects of the invention, and examples include various organic solvents and liquid organic polymers.

Examples of the organic solvents include ketones such as acetone, methyl ethyl ketone (MEK), and methyl isobutyl ketone (MIBK); cyclic ethers such as tetrahydrofuran (THF) and dioxolane; esters such as methyl acetate, ethyl acetate, and butyl acetate; aromatics such as toluene and xylene; and alcohols such as carbitol, cellosolve, methanol, isopropanol, butanol, and propylene glycol monomethyl ether. These can be used singly or in combination; however, above all, methyl ethyl ketone is preferable from the viewpoints of volatility at the time of application and recovery of the solvent.

The liquid organic polymer is a liquid organic polymer that does not directly contribute to a curing reaction, and examples include a carboxyl group-containing polymer modification product (FLOWLEN G-900 and NC-500; KYOEISHA CHEMICAL Co., LTD.), an acrylic polymer (FLOWLEN WK-20; KYOEISHA CHEMICAL Co., LTD.), an amine salt of a special modified phosphoric acid ester (HIPLAAD ED-251; Kusumoto Chemicals, Ltd.), and a modified acrylic block copolymer (DISPERBYK 2000; BYK).

<Resin>

Furthermore, the composition of the invention may have a resin other than the substituted or unsubstituted allyl group-containing maleimide compound of the invention. Regarding the resin, any conventionally known resin may be incorporated to the extent that does not impair the effects of the invention, and for example, a thermosetting resin or a thermoplastic resin can be used.

A thermosetting resin is a resin having the characteristics by which the resin can change to be substantially insoluble and infusible when the resin is cured by means of heating, radiation, a catalyst, or the like. Specific examples thereof include a phenolic resin, a urea resin, a melamine resin, a benzoguanamine resin, an alkyd resin, an unsaturated polyester resin, a vinyl ester resin, a diallyl terephthalate resin, an epoxy resin, a silicone resin, a urethane resin, a furan resin, a ketone resin, a xylene resin, a thermosetting polyimide resin, a benzoxazine resin, an active ester resin, an aniline resin, a cyanate ester resin, a styrene-maleic anhydride (SMA) resin, and a maleimide resin other than the allyl group-containing maleimide compound obtainable by the invention. These thermosetting resins can be used singly or in combination of two or more kinds thereof.

A thermoplastic resin refers to a resin that can be melt-molded by heating. Specific examples thereof include a polyethylene resin, a polypropylene resin, a polystyrene resin, a rubber-modified polystyrene resin, an acrylonitrile-butadiene-styrene (ABS) resin, an acrylonitrile-styrene (AS) resin, a polymethyl methacrylate resin, an acrylic resin, a polyvinyl chloride resin, a polyvinylidenew chloride resin, a polyethylene terephthalate resin, an ethylene-vinyl alcohol resin, a cellulose acetate resin, an ionomer resin, a polyacrylonitrile resin, a polyamide resin, a polyacetal resin, a polybutylene terephthalate resin, a polylactic acid resin, a polyphenylene ether resin, a modified polyphenylene ether resin, a polycarbonate resin, a polysulfone resin, a polyphenylene sulfide resin, a polyetherimide resin, a polyether sulfone resin, a polyallylate resin, a thermoplastic polyimide resin, a polyamideimide resin, a polyether ether ketone resin, a polyketone resin, a liquid crystalline polyester resin, a fluororesin, a syndiotactic polystyrene resin, and a cyclic polyolefin resin. These thermoplastic resins can be used singly or in combination of two or more kinds thereof.

<Curing Agent>

The composition of the invention may use a curing agent in accordance with the compounding substances. Examples include various curing agents such as an amine-based curing agent, an amide-based curing agent, an acid anhydride-based curing agent, a phenolic curing agent, an active ester-based curing agent, a carboxyl group-containing curing agent, and a thiol-based curing agent.

Examples of the amine-based curing agent include diaminodiphenylmethane, diaminodiphenylethane, diaminodiphenyl ether, diaminodiphenylsulfone, ortho-phenylenediamine, meta-phenylenediamine, para-phenylenediamine, meta-xylenediamine, para-xylenediamine, diethyltoluenediamine, diethylenetriamine, triethylenetetramine, isophorone diamine, imidazole, a BF3-amine complex, a guanidine derivative, and a guanamine derivative.

Examples of the amide-based curing agent include dicyandiamide, and a polyamide resin synthesized from a dimer of linolenic acid and ethylenediamine.

Examples of the acid anhydride-based curing agent include phthalic anhydride, trimellitic anhydride, pyromellitic anhydride, maleic anhydride, tetrahydrophthalic anhydride, methyltetrahydrophthalic anhydride, methylnadic anhydride, hexahydrophthalic anhydride, and methylhexahydrophthalic anhydride.

Examples of the phenolic curing agent include polyvalent phenolic compounds such as bisphenol A, bisphenol F, bisphenol S, resorcin, catechol, hydroquinone, fluorene bisphenol, 4,4'-biphenol, 4,4',4"-trihydroxytriphenylmethane, naphthalenediol, 1,1,2,2-tetrakis(4-hydroxyphenyl)ethane, calixarene, a phenol novolac resin, a cresol novolac resin, an aromatic hydrocarbon formaldehyde resin-modified phenolic resin, a dicyclopentadiene-phenol addition type resin, a phenol aralkyl resin (Xylok resin), a polyvalent phenol novolac resin synthesized from a polyvalent hydroxy compound and formaldehyde, which is represented by a resorcin novolac resin, a naphthol aralkyl resin, a trimethylolmethane resin, a tetraphenylolethane resin, a naphthol novolc resin, a naphthol-phenol co-condensed novolac resin, a naphthol-cresol co-condensed novolac resin, a biphenol-modified phenolic resin (polyvalent phenolic compound having a phenol nucleus linked thereto via a bismethylene group), a biphenyl-modified naphthol resin (polyvalent naphthol compound having a phenol nucleus linked thereto via a bismethylene group), an aminotriazine-modified phenolic resin (polyvalent phenolic compound having a phenol nucleus linked thereto via melamine, benzoguanamine, or the like), and an alkoxy group-containing aromatic ring-modified novolac resin (polyvalent phenolic compound having a phenol nucleus and an alkoxy group-containing aromatic ring linked thereto via formaldehyde).

These curing agents may be used singly or in combination of two or more kinds thereof.

Furthermore, the composition of the invention can also use a curing accelerator alone or in combination with the curing agent described above. Regarding the curing accelerator, various compounds that accelerate a curing reaction of a curable resin can be used, and examples thereof include a phosphorus-based compound, a tertiary amine compound, an imidazole compound, an organic acid metal salt, a Lewis acid, and an amine complex salt. Among these, it is preferable to use an imidazole compound, a phosphorus-based compound, or a tertiary amine compound. Particularly, in the case of using the composition for a use application as a semiconductor encapsulating material, from the viewpoint of having excellent curability, heat resistance, electrical characteristics, moisture resistance reliability, and the like, triphenylphosphine and tetraphenylphosphonium tetra-p-tolyl borate are preferred among the phosphorus-based compounds, and 1,8-diazabicyclo[5.4.0]-undecene (DBU) is preferred among tertiary amines.

<Other Compounding Substances>

The composition of the invention may also have other compounding substances. Examples thereof include a catalyst, a polymerization initiator, an inorganic pigment, an organic pigment, an extender pigment, a clay mineral, a wax, a surfactant, a stabilizer, a fluidity adjusting agent, a coupling agent, a dye, a leveling agent, a rheology controlling agent, an ultraviolet absorber, an oxidation inhibitor, a flame retardant, and a plasticizer.

<Cured Product>

A cured product obtainable by curing the composition of the invention undergoes low linear expansion and has a high glass transition temperature and excellent resistance to thermal decomposition, and therefore, the cured product can be used suitably for heat-resistant members or electronic members. The method for molding a cured product is not particularly limited, and the composition may be molded alone, or the composition may also be laminated on a base material to produce a laminate.

In the case of curing the composition of the invention, it is recommended to implement thermal curing. At the time of performing thermal curing, any conventionally known curing catalyst may be used; however, the composition of the invention can be cured even without using a curing catalyst, through a reaction between a maleimide group and an allyl group.

In the case of performing thermal curing, the composition may be cured by heating for once, or the composition may be cured by performing multiple stages of a heating process.

In the case of using a curing catalyst, for example, inorganic acids such as hydrochloric acid, sulfuric acid, and phosphoric acid; organic acids such as p-toluenesulfonic acid, isopropyl monophosphate, and acetic acid; inorganic bases such as sodium hydroxide and potassium hydroxide; titanic acid esters such as tetraisopropyl titanate and tetrabutyl titanate; various compounds containing basic nitrogen atoms, such as 1,8-diazabicyclo[5.4.0]undecene-7 (DBU), 1,5-diazabicyclo[4.3.0]nonene-5 (DBN), 1,4-diazabicyclo[2.2.2]octane (DABCO), tri-n-butylamine, dimethylbenzylamine, monoethanolamine, imidazole, and 1-methylimidazole; various quaternary ammonium salts such as a tetramethylammonium salt, a tetrabutylammonium salt, and a dilauryldimethylammonium salt, the quaternary ammonium salts having chloride, bromide, carboxylate, hydroxide, or the like as counter anions; tin carboxylates such as dibutyltin diacetate, dibutyltin dioctoate, dibutyltin dilaurate, dibutyltin diacetylacetonate, tin octoate, or tin stearate; and organic peroxides such as benzoyl peroxide, cumene hydroperoxide, dicumyl peroxide, lauroyl peroxide, di-t-butyl peroxide, t-butyl hydroperoxide, methyl ethyl ketone peroxide, t-butyl perbenzoate, 2,5-dimethyl-2,5-di(t-butylperoxy)hexyne-3, can be used. The catalysts may be used singly, or two or more kinds thereof may be used in combination.

Furthermore, since the allyl group-containing maleimide compound of the invention has a carbon-carbon double bond, the maleimide compound can also be used for curing by active energy rays in combination. In the case of performing curing by active energy rays, a photopolymerization initiator may be incorporated into the composition. Regarding the photopolymerization initiator, known agents may be used, and for example, one or more selected from the group consisting of acetophenones, benzyl ketals, and benzophenones can be preferably used. Examples of the acetophenones include diethoxyacetophenone, 2-hydroxy-2-methyl-1-phenylpropan-1-one, 1-(4-isopropylphenyl)-2-hydroxy-2-methylpropan-1-one, 4-(2-hydroxyethoxy)phenyl-(2- hydroxy-2-propyl) ketone. Examples of the benzyl ketals include 1-hydroxycyclohexyl-phenyl ketone and benzyl dimethyl ketal. Examples of the benzophenones include benzophenone and methyl o-benzoylbenzoate. Examples of the benzoins include benzoin, benzoin methyl ether, and benzoin isopropyl ether. The photopolymerization initiators may be used singly, or two or more kinds thereof may be used in combination.

In a case in which curing is carried out by using thermal curing and curing by active energy rays in combination, heating and active energy ray irradiation may be carried out simultaneously, or the two may be carried out separately. For example, thermal curing may be carried out after active energy ray irradiation is carried out, or curing by active energy rays may be carried out after thermal curing. Furthermore, the respective curing methods may be carried out two or more times in combination, and the curing method may be selected as appropriate according to the use application.

<Laminate>

The cured product of the invention can be produced into a laminate by laminating the cured product with a base material.

Regarding the base material of the laminate, an inorganic material such as metal or glass; an organic material such as plastic or wood; and the like may be used as appropriate depending on the use application, and the shape of the laminate may be a flat plate, a sheet shape, or a three-dimensional shape having a three-dimensional structure. Any arbitrary shape according to the purpose, such as a shape having a curvature on the entire surface or a portion thereof, may be used. Furthermore, there are no limitations on the hardness, thickness, and the like of the base material. Furthermore, it is also acceptable that the cured product of the invention is used as a base material, and the cured product of the invention is further laminated thereon.

In the case of use applications such as a circuit board and a semiconductor package board, it is preferable to laminate a metal foil, and examples of the metal foil include copper foil, aluminum foil, gold foil, and silver foil. From the viewpoint of having satisfactory processability, it is preferable to use copper foil.

In regard to the laminate of the invention, the cured product layer may be formed by directly applying a composition on the base material, or by molding, and it is also acceptable to laminate a layer that has been molded in advance. In the case of directly applying a composition, the coating method is not particularly limited, and examples thereof include a spray method, a spin coating method, a dipping method, a roll coating method, a blade coating method, a doctor roll method, a doctor blade method, a curtain coating method, a slit coating method, a screen printing method, and an inkjet method. In the case of directly molding the cured product layer, in-mold molding, insert molding, vacuum molding, extrusion lamination molding, press molding, and the like may be used.

In the case of laminating a molded composition, an uncured or semi-cured composition layer may be laminated and then cured, or a cured product layer obtained by completely curing the composition may be laminated on the base material.

Furthermore, it is also acceptable that a precursor that can become a base material is laminated on the cured product of the invention by applying and curing the precursor, or the precursor that can become a base material or the composition of the invention may be adhered to the cured product of the invention in an uncured or semi-cured state and then may be cured. The precursor that can become a base material is not particularly limited, and various curable resin compositions may be used.

<Fiber-Reinforced Resin>

In a case in which the composition of the invention includes a fibrous substrate, and the fibrous substrate is a reinforcing fiber, the composition including the fibrous substrate can be used as a fiber-reinforced resin.

The method for incorporating a fibrous substrate into the composition is not particularly limited as long as the method does not impair the effects of the invention, and examples thereof include methods of compositizing the fibrous substrate and the composition by methods such as kneading, coating, impregnation, injection, and compression. The incorporation method can be selected as appropriate depending on the form of the fiber and the use application of the fiber-reinforced resin.

The method for molding the fiber-reinforced resin of the invention is not particularly limited. When a plate-like product is to be produced, an extrusion molding method is generally used; however, molding can also be achieved by flat surface pressing. In addition to this, it is possible to use an extrusion molding method, a blow molding method, a compression molding method, a vacuum molding method, an injection molding method, and the like. Furthermore, when a film-like product is to be produced, in addition to a melt extrusion method, a solution casting method can be used. In the case of using a melt molding method, examples thereof include inflation film molding, cast molding, extrusion lamination molding, calender molding, sheet molding, fiber molding, blow molding, injection molding, rotational molding, and coating molding. Furthermore, in the case of a resin that is cured by active energy rays, a cured product can be produced by using various curing methods using active energy rays. Particularly, in the case of using a thermosetting resin as a main component of the matrix resin, a molding method of producing a molding material into a prepreg and pressing and heating the prepreg using a press or an autoclave may be used. In addition to this, Resin Transfer Molding (RTM) molding, Vacuum assist Resin Transfer Molding (VaRTM) molding, lamination molding, hand lay-up molding, and the like may be used.

<Prepreg>

The fiber-reinforced resin of the invention can form a state called an uncured or semi-cured prepreg. A cured product may also be formed by distributing a manufactured product in a prepreg state and then performing final curing. In the case of forming a laminate, when a prepreg is formed, subsequently other layers are laminated thereon, and then final curing is performed, a laminate having various layers closely adhered to each other can be formed, which is preferable.

The mass proportions of the composition and the fibrous substrate used at this time is not particularly limited; however, usually, it is preferable to adjust the resin fraction in the prepreg to be 20% to 60% by mass.

<Heat-Resistant Material and Electronic Material>

The substituted or unsubstituted allyl group-containing maleimide compound of the invention is such that since the cured product thereof undergoes low linear expansion and has excellent resistance to thermal decomposition, the cured product can be suitably used for a heat-resistant member or an electronic member. Particularly, the cured product can be suitably used for a semiconductor encapsulating material, a circuit board, a buildup film, a buildup substrate, an adhesive, or a resist material. Furthermore, the substituted or unsubstituted allyl group-containing maleimide compound can also be suitably used for a matrix resin of the fiber-reinforced resin, and is particularly suitable as a highly heat-resistant prepreg. Since the maleimide compound exhibits solubility in various solvents, the maleimide compound can be produced into coating materials. Furthermore, since the maleimide compound can be cured at low temperature compared to conventional heat-resistant coating materials that require high-temperature baking at or above 300° C., the maleimide compound can also be suitably used as a resin for a heat-resistant coating material. A heat-resistant member or electronic member thus obtainable can be suitably used for various use applications, and examples of the applications include, but are not limited to, industrial machine parts, general machine parts, parts for automobiles, railways, vehicles, and the like, aerospace-related parts, electronic and electric parts, construction materials, container and packaging materials, daily goods, sports and leisure goods, and case members for wind power generation.

In the following description, examples of representative products will be described.

1. Semiconductor Encapsulating Material

Regarding a method for obtaining a semiconductor encapsulating material from the composition of the invention, a method of sufficiently melting and mixing the above-mentioned composition, a curing accelerator, and compounding agents such as an inorganic filler, using an extruder, a kneader, rolls, or the like as necessary, until the mixture becomes uniform, may be used. At that time, usually, fused silica is used as the inorganic filler; however, in a case in which the composition of the invention is used as a highly heat-conductive semiconductor encapsulating material for power transistors and power IC's, crystalline silica having higher thermal conductivity than fused silica, high-packaging fillers such as alumina and silicon nitride, or fused silica, crystalline silica, alumina, silicon nitride or the like may be used. Regarding the filling factor, it is preferable to use an inorganic filler in an amount in the range of 30% to 95% by mass with respect to 100 parts by mass of the curable resin composition. Above all, in order to enhance flame retardancy, moisture resistance, and resistance to solder cracking and to promote a decrease in the linear expansion coefficient, the amount of the inorganic filler is more preferably 70 parts by mass or more, and even more preferably 80 parts by mass or more.

2. Semiconductor Device

Regarding semiconductor package molding for obtaining a semiconductor device from the curable resin composition of the invention, a method of casting the semiconductor encapsulating material described above, or molding the semiconductor encapsulating material using a transfer molding machine, an injection molding machine, or the like, and heating the resultant at 50° C. to 250° C. for a time between 2 and 10 hours, may be mentioned.

3. Printed Circuit Board

Regarding a method for obtaining a printed circuit board from the composition of the invention, a method of laminating the above-mentioned prepreg by a conventional method, appropriately overlapping a copper foil, and heating and compressing the laminate at 170° C. to 300° C. at a pressure of 1 to 10 MPa for 10 minutes to 3 hours, may be mentioned.

4. Buildup Substrate

A method for obtaining a buildup substrate from the composition of the invention, for example, the following steps may be mentioned. First, a step of applying the above-described composition, which has been produced by appropriately mixing rubber, a filler, or the like, on a circuit board having a circuit formed thereon using a spray coating method, a curtain coating method, or the like, and then curing the composition (Step 1). A step of subsequently performing perforation of predetermined through-holes and the like as necessary, subsequently treating the cured product with a roughening agent, forming concavities and convexities by rinsing the surface with hot water, and subjecting a metal such as copper to a plating treatment (Step 2). A step of sequentially repeating these operations as desired, and forming a resin insulating layer and a conductor layer of a predetermined circuit pattern by alternately building up the layers (Step 3). Incidentally, perforation of through-holes is performed after the formation of a resin insulating layer as the outermost layer. Furthermore, the buildup substrate of the invention can also be produced by compressing, under heating at 170° C. to 300° C., a resin-attached copper foil obtained by semi-curing the resin composition on a copper foil, on a wiring board having a circuit formed thereon, while omitting a process of forming a roughened surface and subjecting the surface to a plating treatment.

5. Buildup Film

Regarding a method for obtaining a buildup film from the composition of the invention, a buildup film can be produced by applying the above-described composition on the surface of a supporting film (Y) as a base material, drying the organic solvent by heating, blowing hot air, or the like, and thereby forming a layer (X) of the composition.

Regarding the organic solvent to be used herein, it is preferable to use ketones such as acetone, methyl ethyl ketone, and cyclohexanone; acetic acid esters such as ethyl acetate, butyl acetate, cellosolve acetate, propylene glycol monomethyl ether acetate and carbitol acetate; carbitols such as cellosolve and butyl carbitol; aromatic hydrocarbons such as toluene and xylene; dimethylformamide, dimethylacetamide, N-methylpyrrolidone; and the like. Furthermore, it is preferable to use the organic solvent at a proportion that makes a non-volatile fraction of 30% to 60% by mass.

The thickness of the layer (X) thus formed is usually adjusted to be greater than or equal to the thickness of the conductor layer. Since the thickness of the conductor layer carried by a circuit board is usually in the range of 5 to 70 μm, it is preferable that the thickness of the resin composition layer has a thickness of 10 to 100 μm. Incidentally, the layer (X) of the composition according to the invention may be protected with a protective film that will be mentioned below. By protecting the layer with a protective film, adhesion of contaminants or scratches to the resin composition layer surface can be prevented.

Examples of the supporting film and the protective film described above include films of polyolefins such as polyethylene, polypropylene, and polyvinyl chloride; polyesters such as polyethylene terephthalate (hereinafter, may be abbreviated to "PET"), and polyethylene naphthalate; polycarbonate, and polyimide; as well as release paper, and metal foils such as copper foil and aluminum foil. Incidentally, the supporting film and the protective film may also be subjected to a release treatment in addition to a mad treatment and a corona treatment. The thickness of the supporting film is not particularly limited; however, the thickness is usually 10 to 150 μm, and preferably in the range of 25 to 50 μm. Furthermore, the thickness of the protective film is preferably set to 1 to 40 μm.

The above-described supporting film (Y) is detached after the buildup film is laminated on a circuit board, or after an insulating layer is formed by heating and curing the composition. When the supporting film (Y) is detached after a curable resin composition layer that constitutes the buildup film is heated and cured, adhesion of contaminants and the like during the curing process can be prevented. In the case of detaching the supporting film after being cured, the supporting film is usually subjected to a release treatment in advance.

Using a buildup film obtained as described above, a multilayer printed circuit board can be produced. For example, in a case in which the layer (X) is protected with a protective film, these layers are detached, and then the layer (X) is laminated on one surface or on both surfaces of a circuit board so as to come into direct contact with the circuit board, for example, by a vacuum lamination method. The method for lamination may be of batch type or of continuous type using rolls. Furthermore, as necessary, it is also acceptable to have the buildup film and the circuit board heated (pre-heated) as necessary, before lamination is performed. Regarding the conditions for lamination, it is preferable to set the compression temperature (lamination temperature) to 70° C. to 140° C., and it is preferable to set the compression pressure to 1 to 11 kgf/cm$^2$ (9.8×10$^4$ to 107.9× 10$^4$ N/m$^2$). It is preferable to perform lamination under reduced pressure by setting the air pressure to be 20 mmHg (26.7 hPa) or less.

6. Conductive Paste

Regarding a method for obtaining a conductive paste from the composition of the invention, for example, a method of dispersing electroconductive particles in the composition may be mentioned. The conductive paste can be produced into a paste resin composition for circuit connection or an anisotropic conductive adhesive, depending on the type of the electroconductive particles used.

EXAMPLES

Next, the present invention will be specifically described by way of Examples and Comparative Examples, and in the following description, unless particularly stated otherwise, the units "parts" and "percent (%)" are on a mass basis.

Incidentally, high performance liquid chromatography (HPLC), $^1$H— and $^{13}$C-NMR, MS spectroscopy, and differential scanning calorimetry (DSC) were measured under the following conditions.

HPLC
 Apparatus: "LC1260" manufactured by Agilent Technologies, Inc.
 Developing solvent: Shown in the following Table 1
 Detector: Photodiode array detector
 Flow rate: 1.0 mL/min
 Column used: Poroshell 120 EC-C18

TABLE 1

| Time (minutes) | 0 | 1.67 | 5.00 | 8.00 | 9.33 | 10.0 |
|---|---|---|---|---|---|---|
| Water | 70 | 70 | 10 | 10 | 70 | 70 |
| Acetonitrile | 30 | 30 | 90 | 90 | 30 | 30 |

$^1$H-NMR
 Apparatus: "JNM-ECA600" manufactured by JEOL RESONANCE Inc.
 Magnetic field intensity: 600 MHz
 Cumulative number: 32 times
 Solvent: DMSO-d$_6$
 Sample concentration: 30% by mass
$^{13}$C-NMR
 Apparatus: "JNM-ECA600" manufactured by JEOL RESONANCE Inc.
 Magnetic field intensity: 150 MHz
 Cumulative number: 320 times
 Solvent: DMSO-d$_6$
 Sample concentration: 30% by mass
FD-MS
 Apparatus: "JMS-T100GC AccuTOF" manufactured by JEOL Ltd.
 Measurement range: m/z=50.00 to 2000.00
 Change rate: 25.6 mA/min
 Final current value: 40 mA
 Cathode voltage: −10 kV
DSC
 Apparatus: "DSC7000X" manufactured by Hitachi High-Technologies Corporation
 Atmosphere: Nitrogen
 Heating program: Maintained for 5 minutes at 30° C.→heating rate 10° C./min→maintained for 2 minutes at 350° C.

<Example 1> Synthesis of Allyl Group-Containing Maleimide Compound A (1-1) Protection of Amino Group 50.10 g (0.132 mol) of 9,9-bis (3-amino-4-hydroxyphenyl) fluorene (BAHF, manufactured by JFE Chemical Corporation), 580 mL of N,N-dimethylformamide (DMF), 170 mL of ion-exchanged water, and 33.72 g (0.330 mol) of acetic anhydride were introduced into a 1-L flask equipped with a thermometer, a cooling tube, and a stirrer, and the mixture was reacted for 2 hours at 60° C. Subsequently, the reaction mixture was air-cooled to room temperature. A precipitate was filtered and washed with ion-exchanged water, and then a powder thus obtained was dried in a vacuum for 8 hours at 80° C. Thus, 42.30 g (yield 68.9%) of reaction product (a-1) was obtained.

(1-2) Introduction of Substituted or Unsubstituted Allyl Group 41.91 g (0.090 mmol) of (a-1) and 500 mL of DMF were introduced into a 1-L flask equipped with a thermometer, a cooling tube, and a stirrer, and the mixture was stirred. Next, 27.97 g (0.202 mol) of potassium carbonate was added thereto, and the reaction liquid was heated to 60° C. Subsequently, 24.66 g (0.204 mol) of allyl bromide was slowly added dropwise thereto. After completion of dropwise addition, the mixture was allowed to react for 8.5 hours at 60° C. and then was air-cooled to room temperature. The reaction liquid was filtered, and then reprecipitation was performed with ion-exchanged water. A wet cake was separated by filtration and washed with ion-exchanged water, and then the wet cake was dried in a vacuum for 12 hours at 80° C. Thus, 46.12 g (yield 94.0%) of (a-2) was obtained as a powder.

(1-3) Deprotection 44.83 g (0.082 mol) of (a-2) and 120 mL of ethanol were introduced into a 500-mL flask equipped with a thermometer, a cooling tube, and a stirrer, and the mixture was stirred. 52.91 g of concentrated hydrochloric acid was added thereto, and the mixture was heated to 60° C. The mixture was allowed to react for 9 hours at 60° C. and then air-cooled to room temperature. The reaction liquid was neutralized with a 20% aqueous solution of sodium hydroxide, and then the resultant was extracted with ethyl acetate. The extract was washed with ion-exchanged water, sodium sulfate was added thereto, and the mixture was dried and then concentrated under reduced pressure. Furthermore, the residue was dried in a vacuum for 12 hours at 80° C. Thus, 28.51 g (yield 75.2%) of (a-3) was obtained as a solid.

(1-4) Maleimidation 13.51 g (0.138 mol) of maleic anhydride and 400 mL of toluene were introduced into a 1-L flask equipped with a thermometer, a cooling tube, a Dean-Stark trap, and a stirrer, and the mixture was stirred at room temperature. Next, a mixed solution of 28.51 (0.062 mmol) g of (a-3) and 40 mL of DMF was added dropwise thereto for 30 minutes. After completion of dropwise addition, the mixture was allowed to react for another 2 hours at room temperature. 2.18 g of p-toluenesulfonic acid monohydrate was added thereto, the reaction liquid was heated, and water and toluene that had been azeotropically heated to reflux were cooled and separated. Subsequently, only toluene was returned into the system, and a dehydration reaction was carried out for 12 hours. The reaction mixture was air-cooled to room temperature, and then a precipitate was separated by filtration. The precipitate was dried in a vacuum for 12 hours at 80° C., and thus 16.95 g (yield 44.1%) of allyl group-containing maleimide compound A was obtained.

The $^1$H-NMR, $^{13}$C-NMR and MS spectra of the allyl group-containing maleimide compound A thus obtained were measured, and the compound was subjected to HPLC to determine the purity. The following results were obtained.

$^1$H-NMR: δ7.93 ppm (2H), 7.46-7.32 ppm (6H), 7.15-7.00 ppm (10H), 5.91-5.82 ppm (2H), 5.24-5.13 ppm (4H), 4.51 ppm (4H);

$^{13}$C-NMR: δ169.73 ppm, 152.86 ppm, 150.26 ppm, 139.34 ppm, 137.52 ppm, 134.89 ppm, 133.01 ppm, 129.30 ppm, 128.08 ppm, 127.87 ppm, 125.83 ppm, 120.67 ppm, 119.90 ppm, 116.78 ppm, 113.22 ppm, 68.32 ppm, 63.23 ppm;

MS spectroscopy: M$^+$=620;

Purity: 95.8% (HPLC area %, detection wavelength: 275 nm)

[Chem. 21]

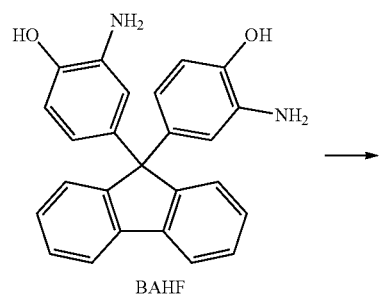

BAHF

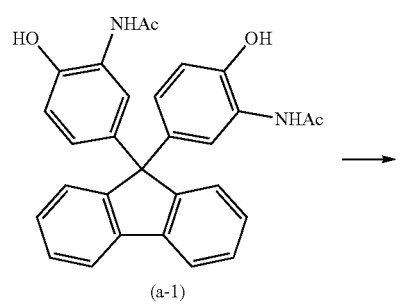

(a-1)

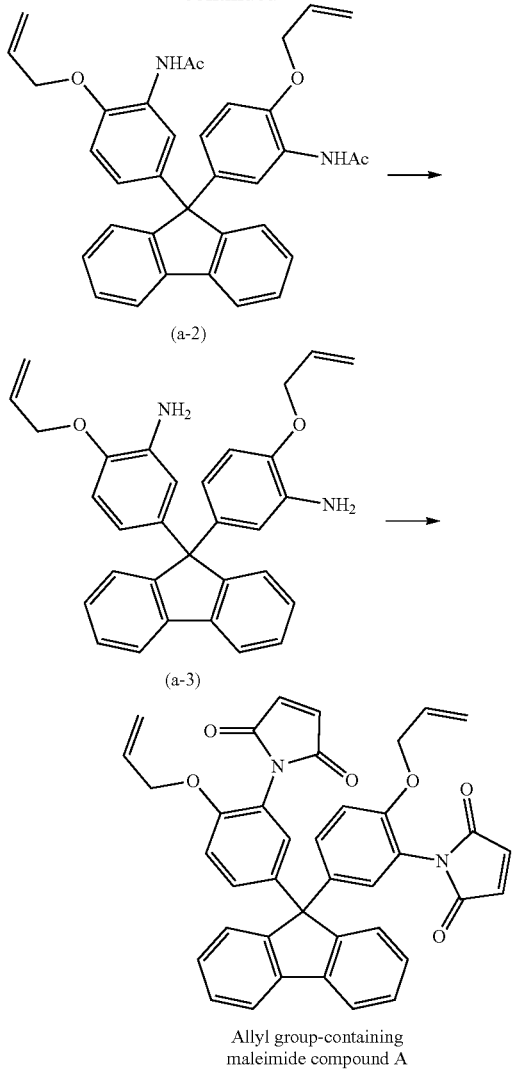

Allyl group-containing maleimide compound A

<Example 2> Synthesis of Allyl Group-Containing Maleimide Compound B 193.04 g (1.59 mol) of 2,6-dimethylaniline and 58.82 g of 6 mol/L hydrochloric acid were introduced into a 500-mL flask equipped with a thermometer, a cooling tube, and a stirrer, and the mixture was stirred. The reaction liquid was heated to a reflux state, and then a mixed solution of 48.61 g (0.40 mol) of 4-hydroxybenzaldehyde and 50 mL of DMF was slowly added dropwise thereto. After completion of dropwise addition, the mixture was allowed to react under reflux for 20 hours, and then the reaction mixture was air-cooled to 60° C. The reaction mixture was neutralized with a 20% aqueous solution of sodium hydroxide, and the supernatant was removed by decantation. Methanol was added to the residue, and a uniform solution was obtained. Subsequently, reprecipitation was performed with ion-exchanged water. A precipitate was separated by filtration and washed with ion-exchanged water, and the precipitate was dried in a vacuum for 12 hours at 80° C. Thus, 116.81 g (yield 84.7%) of a hydroxy group-containing diamine represented by the following Formula (b) was obtained as a powder.

[Chem. 22]

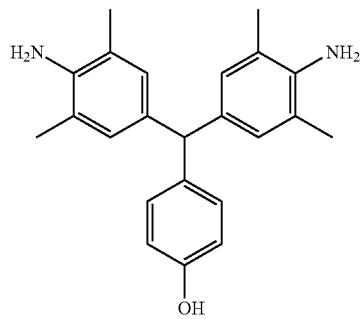

(b)

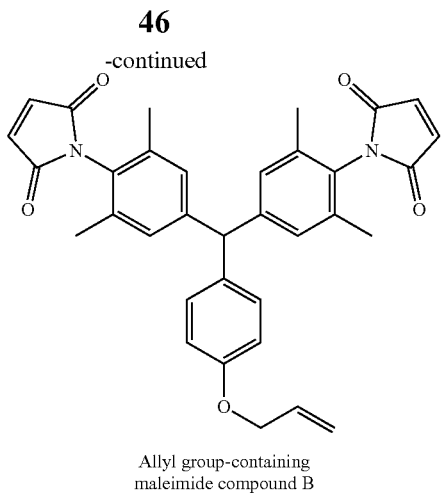

Allyl group-containing
maleimide compound B

Allyl group-containing maleimide compound B was obtained by a method similar to that of Example 1, except that the hydroxy group-containing diamine represented by Formula (b) was used instead of BAHF, and the molar ratio was appropriately adjusted. Incidentally, the $^1$H-NMR, $^{13}$C-NMR, MS spectra, and DSC of the allyl group-containing maleimide compound B were measured, and the maleimide compound was subjected to HPLC to determine the purity. The following results were obtained.

$^1$H-NMR: δ7.24 ppm (4H), 7.10 ppm (2H), 6.99 ppm (4H), 6.92 ppm (2H), 6.07-6.00 ppm (1H), 5.50 ppm (1H), 5.40 ppm (1H), 5.24 ppm (1H), 4.54 ppm (2H), 1.98 ppm (12H);

$^{13}$C-NMR: δ169.86 ppm, 156.71 ppm, 144.70 ppm, 136.73 ppm, 135.00 ppm, 134.90 ppm, 133.77 ppm, 129.99 ppm, 128.71 ppm, 127.75 ppm, 117.47 ppm, 114.62 ppm, 68.15 ppm, 54.40 ppm, 17.60 ppm;

MS spectroscopy: M$^+$=546;

Melting point (DSC peak top): 246° C.;

Purity: 99.9% (HPLC area %, detection wavelength: 275 nm)

[Chem. 23]

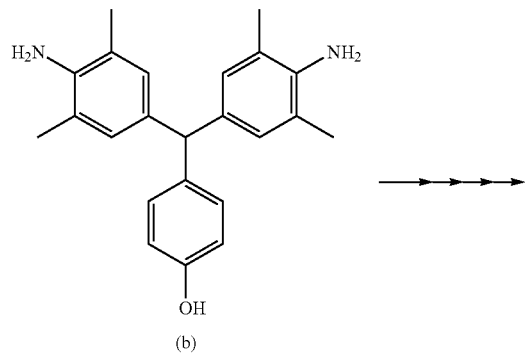

(b)

<Example 3> Synthesis of Allyl Group-Containing Maleimide Compound C 45.12 g (0.299 mol) of p-nitrobenzaldehyde, 76.46 g (0.626 mol) of 2,6-dimethylphenol, and 140 mL of toluene were introduced into a 500-mL flask equipped with a thermometer, a cooling tube, a Dean-Stark trap, and a stirrer, and the mixture was stirred. 5.78 g of p-toluenesulfonic acid monohydrate was added thereto, the reaction liquid was allowed to react, and water and toluene that had been azeotropically heated to reflux were cooled and separated. Subsequently, only toluene was returned into the system, and a dehydration reaction was carried out for 2.5 hours. The reaction mixture was air-cooled to 80° C., and then the reaction liquid was neutralized with a 10% aqueous solution of sodium hydroxide. The neutralized reaction liquid was extracted with toluene. The extract was washed with ion-exchanged water and dried by adding sodium sulfate thereto. The residue was concentrated under reduced pressure, and thus a deep red-colored liquid was obtained. The liquid was dried in a vacuum for 12 hours at 80° C., and thus 105.41 g (yield 93.3%) of a dihydroxy group-containing nitro compound represented by the following Formula (c-0) was obtained as an orange-colored solid.

[Chem. 24]

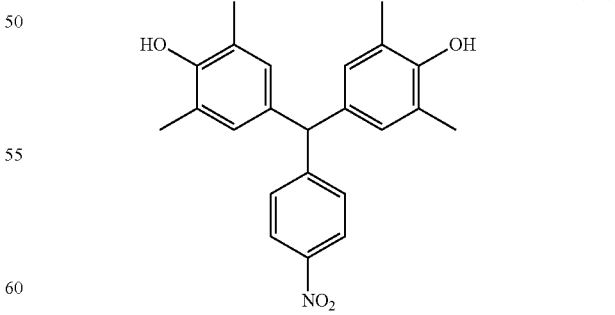

(c-0)

105.00 g (0.278 mol) of the dihydroxy group-containing nitro compound represented by Formula (c-0), 14.80 g of 10% palladium-supported carbon (Pd/C), and 800 mL of ethanol were introduced into a 2-L flask equipped with a thermometer, a cooling tube, and a stirrer, and the mixture was stirred at room temperature. The reaction liquid was heated, and in a hydrogen atmosphere, a hydrogen reduction reaction was carried out for 12 hours at 70° C. The reaction liquid was filtered, and then the filtrate was concentrated under reduced pressure. Subsequently, the concentrated filtrate was dried in a vacuum for 12 hours at 80° C., and thus, 86.99 g (yield 89.9%) of a dihydroxy group-containing amino compound represented by the following Formula (c) was obtained in a powder form.

[Chem. 25]

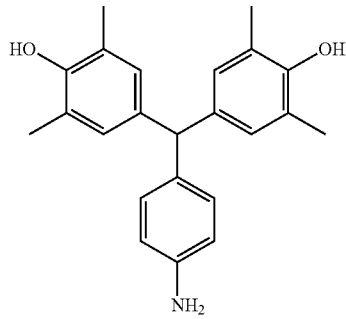

(c)

A crude product of the allyl group-containing maleimide compound C was obtained by a method similar to that of Example 1, except that the molar ratio was appropriately adjusted by using the dihydroxy group-containing amino compound represented by Formula (c) instead of BAHF. The allyl group-containing maleimide compound C was obtained by subjecting the crude product thus obtained to separation and purification by silica gel column chromatography (developing solvent: ethyl acetate/hexane=25/75, volume ratio). Incidentally, the $^1$H-NMR, $^{13}$C-NMR, MS spectra, and DSC of the allyl group-containing maleimide compound A thus obtained were measured, and the maleimide compound was subjected to HPLC to determine the purity. Thus, the following results were obtained.

$^1$H-NMR: δ7.26-7.20 ppm (4H), 7.17 ppm (2H), 6.81 ppm (4H), 6.08-6.04 ppm (2H), 5.43-5.40 ppm (3H), 5.22 ppm (2H), 4.27 ppm (4H), 2.16 ppm (12H);

$^{13}$C-NMR: δ169.97 ppm, 153.91 ppm, 143.81 ppm, 138.73 ppm, 134.65 ppm, 134.55 ppm, 130.22 ppm, 129.43 ppm, 129.32 ppm, 129.13 ppm, 126.57 ppm, 116.78 ppm, 72.46 ppm, 54.48 ppm, 16.20 ppm;

MS spectroscopy: M$^+$=507;

Melting point (DSC peak top): 147° C.;

Purity: 92.4% (HPLC area %, detection wavelength: 254 nm)

[Chem. 26]

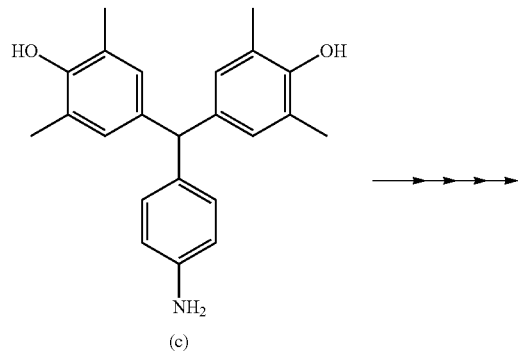

(c)

⟶⟶

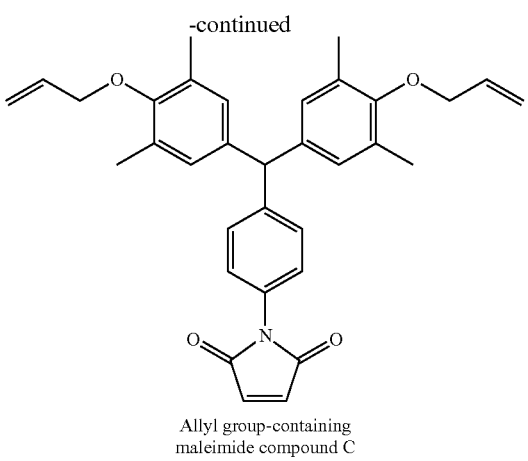

Allyl group-containing maleimide compound C

<Example 4> Synthesis of Allyl Group-Containing Maleimide Compound D 55.33 g (0.449 mol) of 2-methoxyaniline was introduced into a 200-mL flask equipped with a thermometer, a cooling tube, and a stirrer, and the mixture was heated with stirring to 100° C. A mixed solution of 23.86 g (0.225 mol) of benzaldehyde and 11.89 g of concentrated hydrochloric acid was slowly added dropwise thereto. After completion of dropwise addition, the mixed solution was allowed to react for 5 hours at 100° C., and then the reaction liquid was air-cooled to 70° C. The reaction liquid was neutralized with a 20% aqueous solution of sodium hydroxide and then was extracted with ethyl acetate. The extract was washed with ion-exchanged water and dried by adding sodium sulfate thereto. Subsequently, the residue was concentrated under reduced pressure, and thus 66.97 g (yield 88.9%) of a dimethoxy group-containing diamino compound represented by the following Formula (d-0) was obtained.

[Chem. 27]

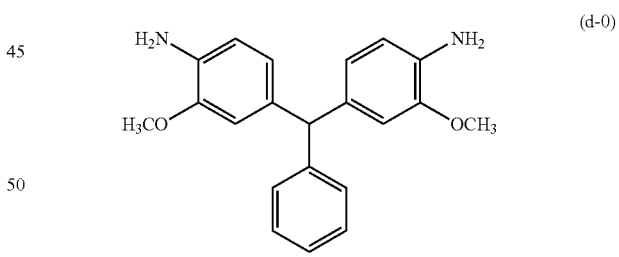

(d-0)

66.00 g (0.197 mol) of the dimethoxy group-containing diamino compound represented by Formula (d-0), 680 mL of acetic acid, and 680 mL of hydrobromic acid (47%) were introduced into a 2-L flask equipped with a thermometer, a cooling tube, and a stirrer, and the mixture was heated with stirring to a reflux state. The mixture was allowed to react for 8 hours under reflux and then was air-cooled to room temperature. The reaction liquid was neutralized with a 20% aqueous solution of sodium hydroxide and then was extracted with ethyl acetate. The extract was washed with ion-exchanged water and dried by adding sodium sulfate thereto. Subsequently, the residue was concentrated under reduced pressure, and thus 55.28 g (yield 91.4%) of a dihydroxy group-containing diamino compound represented by the following Formula (d) was obtained.

[Chem. 28]

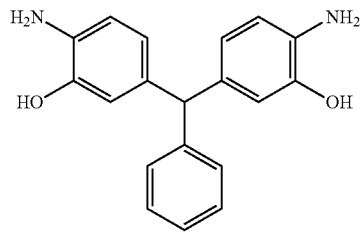

(d)

A crude product of the allyl group-containing maleimide compound C was obtained by a method similar to that of Example 1, except that the molar ratio was appropriately adjusted by using the dihydroxy group-containing diamino compound represented by Formula (d) instead of BAHF. The crude product thus obtained was subjected to separation and purification by silica gel column chromatography (developing solvent: ethyl acetate/hexane=1/1, volume ratio), and thereby an allyl group-containing maleimide compound D was obtained. Incidentally, the $^1$H-NMR, $^{13}$C-NMR, MS spectra, and DSC of the allyl group-containing maleimide compound A thus obtained were measured, and the maleimide compound was subjected to HPLC to determine the purity. The following results were obtained.

$^1$H-NMR: δ7.38-7.14 ppm (11H), 6.96 ppm (2H), 6.83-6.80 ppm (2H), 5.86-5.76 ppm (2H), 5.71 ppm (1H), 5.18-5.11 ppm (4H), 4.47-4.45 ppm (4H);

$^{13}$C-NMR: δ169.92 ppm, 153.85 ppm, 145.86 ppm, 142.86 ppm, 134.99 ppm, 132.87 ppm, 130.24 ppm, 128.99 ppm, 128.50 ppm, 126.59 ppm, 121.29 ppm, 118.45 ppm, 117.06 ppm, 114.33 ppm, 68.33 ppm, 55.70 ppm;

MS spectroscopy: M$^+$=546;

Melting point (DSC peak top): 60° C.;

Purity: 95.8% (HPLC area %, detection wavelength: 275 nm)

[Chem. 29]

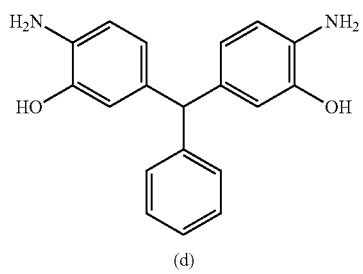

(d)

⇢⇢⇢

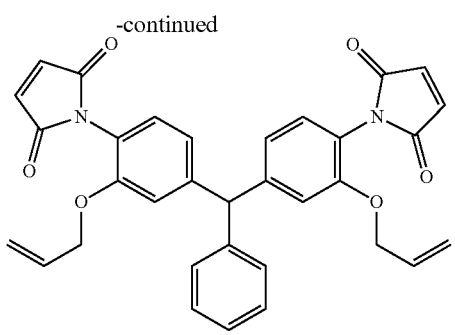

Allyl group-containing maleimide compound D

<Example 5> Synthesis of Allyl Group-Containing Maleimide Compound E 198.27 g (1.00 mol) of 4,4'-diaminodiphenylmethane and 248.28 g (2.00 mol) of 4-hydroxybenzyl alcohol were introduced into a 1-L flask equipped with a thermometer, a cooling tube, a Dean-Stark trap, and a stirrer, and the mixture was heated to 140° C. The mixture was stirred while being dehydrated in a molten state. The mixture was allowed to react for 7 hours at the same temperature and then was air-cooled to room temperature. Thus, 385.89 g of a solid containing a dihydroxy group-containing diamino compound represented by the following Formula (e) as a main component was obtained. Incidentally, the MS spectrum and DSC of the dihydroxy group-containing diamino compound represented by Formula (e) thus obtained were measured, and the following results were obtained.

MS spectroscopy: M$^+$=410

Purity: 26.0% (HPLC area %, detection wavelength: 254 nm)

[Chem. 30]

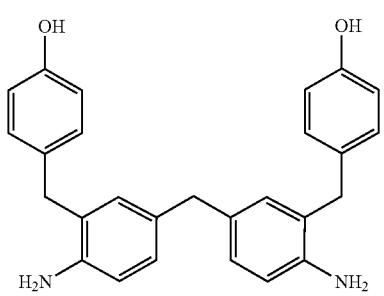

(e)

An allyl group-containing maleimide compound E was obtained by a method similar to that of Example 1, except that the molar ratio was appropriately adjusted by using the dihydroxy group-containing diamino compound represented by Formula (e) instead of BAHF.

[Chem. 31]

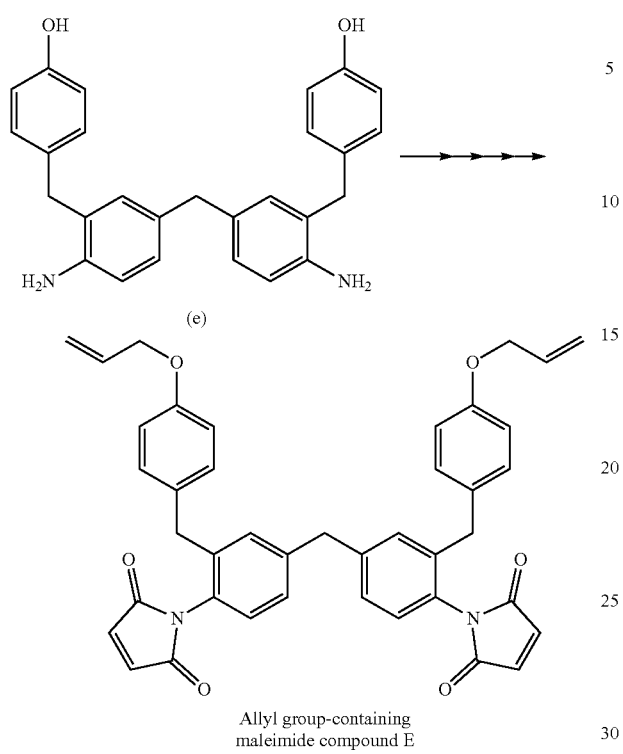

(e)

Allyl group-containing maleimide compound E

<Comparative Example 1> Synthesis of Bismaleimide A 50.85 g (0.519 mol) of maleic anhydride and 930 mL of toluene were introduced into a 2-L flask equipped with a thermometer, a cooling tube, a Dean-Stark trap, and a stirrer, and the mixture was stirred at room temperature. Next, a mixed solution of 50.09 g (0.236 mol) of 4,4'-diamino-2,2'-dimethylbiphenyl (m-TB, manufactured by Wakayama Seika Kogyo Co., Ltd.) and 110 mL of DMF was added dropwise thereto for one hour. After completion of dropwise addition, the mixture was allowed to react for another 2 hours at room temperature. 7.08 g of p-toluenesulfonic acid monohydrate was added thereto, the reaction liquid was heated, and water and toluene that had been azeotropically heated to reflux were cooled and separated. Subsequently, only toluene was returned into the system, and a dehydration reaction was carried out for 22 hours. The resultant was air-cooled to room temperature and then concentrated under reduced pressure, and thus 151.40 g of a yellow wet cake was obtained. The wet cake was dissolved in DMF, and reprecipitation was carried out with ion-exchanged water. A precipitate was separated by filtration and washed with ion-exchanged water, and the precipitate was dried in a vacuum for 12 hours at 80° C. Thus, 84.07 g (yield 95.8%) of bismaleimide A was obtained as a yellow powder. Incidentally, the $^1$H-NMR, $^{13}$C-NMR, MS spectra, and DSC of the bismaleimide A thus obtained were measured, and the compound was subjected to HPLC to determine the purity. The following results were obtained.

$^1$H-NMR: δ7.31 ppm (2H), 7.24-7.21 ppm (8H), 2.07 ppm (6H);

$^{13}$C-NMR: δ170.01 ppm, 139.67 ppm, 136.10 ppm, 134.72 ppm, 130.74 ppm, 129.57 ppm, 127.97 ppm, 124.15 ppm, 19.58 ppm;

MS spectroscopy: M$^+$=372;
Melting point (DSC peak top): 194° C.;
Purity: 91.6% (HPLC area %, detection wavelength: 254 nm)

[Chem. 32]

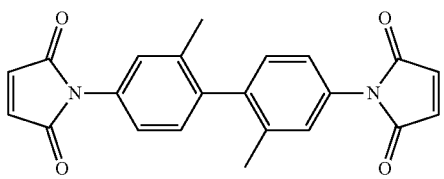

Bismaleimide A

<Comparative Example 2> Synthesis of Bismaleimide B 11.09 g (0.113 mol) of maleic anhydride and 190 mL of toluene were introduced into a 500-mL flask equipped with a thermometer, a cooling tube, a Dean-Stark trap, and a stirrer, and the mixture was stirred at room temperature. Next, a mixed solution of 15.02 g (0.051 mol) of 1,3-bis(4-aminophenoxy)benzene (TPE-R, manufactured by Wakayama Seika Kogyo Co., Ltd.) and 30 mL of DMF was added dropwise thereto for one hour. After completion of dropwise addition, the mixture was allowed to react for another 2 hours at room temperature. 1.07 g of p-toluenesulfonic acid monohydrate was added thereto, the reaction liquid was heated, and water and toluene that had been azeotropically heated to reflux were cooled and separated. Subsequently, only toluene was returned into the system, and a dehydration reaction was carried out for 9 hours. The reaction mixture was air-cooled to room temperature and then concentrated under reduced pressure. A reaction liquid thus obtained was subjected to reprecipitation with ion-exchanged water. A precipitate was separated by filtration and washed with ion-exchanged water, and then the precipitate was dried in a vacuum for 12 hours at 80° C. Thus, 21.90 g (yield 94.2%) of bismaleimide B was obtained as a yellow powder. Incidentally, the $^1$H-NMR, $^{13}$C-NMR, MS spectra, and DSC of the bismaleimide A thus obtained were measured, and the maleimide compound was subjected to HPLC to determine the purity. The following results were obtained.

$^1$H-NMR: δ7.45-7.33 ppm (5H), 7.17-7.14 ppm (8H), 6.84-6.75 ppm (3H);

$^{13}$C-NMR: δ169.94 ppm, 157.78 ppm, 155.45 ppm, 134.65 ppm, 131.33 ppm, 128.60 ppm, 127.03 ppm, 119.03 ppm, 113.79 ppm, 109.47 ppm;

MS spectroscopy: M$^+$=452;
Melting point (DSC peak top): 160° C.;
Purity: 96.3% (HPLC area %, detection wavelength: 254 nm)

[Chem. 33]

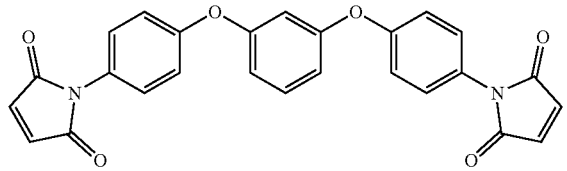

Bismaleimide B

Comparative Example 3

As Comparative Example 3, BMI-1000 (4,4'-diphenylmethanebismaleimide, manufactured by Daiwa Kasei Industry Co., Ltd.) represented by the following formula was used.

[Chem. 34]

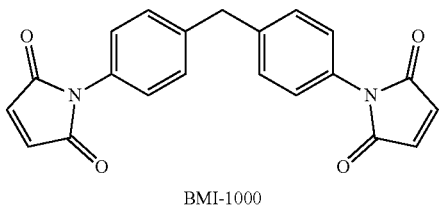

BMI-1000

[Evaluation]

Various evaluations were carried out using the allyl group-containing maleimide compounds of Examples 3 to 5 and the maleimide compounds of Comparative Examples 1 to 3. Incidentally, in the following evaluations, the allyl group-containing maleimide compounds of Examples 3 to 5 and the maleimide compounds of Comparative Examples 1 to 3 will be collectively referred to simply as "maleimide compounds".

<Composition and Cured Product Thereof>

A composition including a maleimide compound was produced, and the composition was cured to produce a cured product.

(Production of Composition and Cured Product)

Compositions 1 to 8 were produced by mixing components according to the following Table 2. Furthermore, the compositions 1 to 8 thus obtained were cured under the following conditions, and cured products 1 to 8 were produced.

However, in regard to the compositions 4 to 6 and 8, when the cured products were produced, the compositions did not melt partially or entirely. Thus, cured products 4 to 6 and 8 could not be produced, and therefore, the evaluation of the glass transition temperature, linear expansion coefficient, and resistance to thermal decomposition could not be carried out.

Curing conditions: Heating for 2 hours at 170° C., for 2 hours at 200° C., and for 2 hours at 250° C.

Cured product plate thickness: 2.4 mm

TABLE 2

| | Maleimide compound | | Other resin | |
|---|---|---|---|---|
| | Type | Amount of incorporation (g) | Type* | Amount of incorporation (g) |
| Composition 1 | Example 3 | 10 | | |
| Composition 2 | Example 4 | 10 | | |
| Composition 3 | Example 5 | 10 | | |
| Composition 4 | Comparative Example 1 | 10 | | |
| Composition 5 | Comparative Example 2 | 10 | | |
| Composition 6 | Comparative Example 1 | 5.5 | BPA-DA | 4.5 |
| Composition 7 | Comparative Example 2 | 5.9 | BPA-DA | 4.1 |
| Composition 8 | Comparative Example 3 | 5.4 | BPA-DA | 4.6 |

*The details of the product names are as follows.
BPA-DA: Bisphenol A diallyl ether (manufactured by Gun Ei Chemical Industry Co., Ltd.)

(Glass Transition Temperature)

Each of the cured products 1 to 8 thus produced (thickness: 2.4 mm) was cut out into a size of 5 mm in width and 54 mm in length, and this was used as a test specimen. For this test specimen, the temperature at which the change in elastic modulus became the maximum (tan δ change ratio was the largest) was evaluated as the glass transition temperature, using a viscoelasticity analyzer (DMA: solid viscoelasticity analyzer "DMS7100" manufactured by Hitachi High-Technologies Corporation, deformation mode: double-supported bending, measurement mode: sinusoidal oscillation, frequency: 1 Hz, rate of temperature increase: 3° C./min). The results thus obtained are presented in the following Table 3.

(Linear Expansion Coefficient)

Each of the cured products 1 to 8 thus produced (thickness: 2.4 mm) was cut out into a size of 5 mm in width and 5 mm in length, and this was used as a test specimen. For this test specimen, the expansion rate in the range of 40° C. to 60° C. was measured using a thermomechanical analyzer ("TMA/SS7100" manufactured by Hitachi High-Technologies Corporation, rate of temperature increase: 3° C./min). The results thus obtained are presented in the following Table 3.

(Resistance to Thermal Decomposition)

Each of the cured products 1 to 8 thus produced (thickness: 2.4 mm) was finely cut, and measurement was performed using a thermal gravity analyzer ("TG/DTA6200" manufactured by Seiko Instruments Inc.) in a nitrogen atmosphere at a rate of temperature increase of 5° C./min. Thus, the temperature at which the weight decreased by 5% (Td5) was determined. The results thus obtained are presented in the following Table 3.

TABLE 3

| | Glass transition temperature (° C.) | Linear expansion coefficient (ppm) | Resistance to thermal decomposition (° C.) |
|---|---|---|---|
| Cured product 1 | 294 | 56 | 376 |
| Cured product 2 | >350 | 53 | 425 |
| Cured product 3 | 288 | 46 | 407 |
| Cured product 4 | Not measurable | Not measurable | Not measurable |
| Cured product 5 | Not measurable | Not measurable | Not measurable |
| Cured product 6 | Not measurable | Not measurable | Not measurable |
| Cured product 7 | 217 | 48 | 391 |
| Cured product 8 | Not measurable | Not measurable | Not measurable |

<Fibrous Substrate-Containing Composition and Cured Product Thereof>

Compositions including a maleimide compound and glass fibers as a fibrous substrate were produced, and the compositions were cured to produce cured products.

For the cured products thus obtained, the flexural modulus, bending strength, and bending strain were evaluated.

(Production of Composition and Cured Product)

Compositions 9 to 16 were produced by mixing components according to the following Table 4. At this time, T-725H (glass fiber for molding materials, manufactured by Nippon Electric Glass Co., Ltd.) was used as a glass fiber.

Furthermore, the compositions 9 to 16 thus obtained were cured under the following conditions, and thus cured products 9 to 16 were produced.

However, in regard to the compositions 12 to 14 and 16, when cured products were produced, the compositions did not melt partially or entirely, and thus, cured products 12 to 14 and 16 could not be produced. Therefore, the evaluation of flexural modulus, bending strain, and bending strength could not be carried out.

Curing conditions: Heating for 2 hours at 170° C., for 2 hours at 200° C., and for 2 hours at 250° C.

Cured product plate thickness: 2.4 mm

TABLE 4

| | Maleimide compound | | Other resin | | Glass fiber |
|---|---|---|---|---|---|
| | Type | Amount of incorporation (g) | Type* | Amount of incorporation (g) | Amount of incorporation (g) |
| Composition 9 | Example 3 | 70 | | | 30 |
| Composition 10 | Example 4 | 70 | | | 30 |
| Composition 11 | Example 5 | 70 | | | 30 |
| Composition 12 | Comparative Example | 70 | | | 30 |
| Composition 13 | Comparative Example 2 | 70 | | | 30 |
| Composition 14 | Comparative Example 1 | 39 | BPA-DA | 31 | 30 |
| Composition 15 | Comparative Example 2 | 41 | BPA-DA | 29 | 30 |
| Composition 16 | Comparative Example 3 | 38 | BPA-DA | 32 | 30 |

*The details of the product names are as follows.
BPA-DA: Bisphenol A diallyl ether (manufactured by Gun Ei Chemical Industry Co., Ltd.)

(Flexural Modulus, Bending Strain, Bending Strength)

In regard to the cured products 9 to 16, a bending test was performed according to JIS-K6911:2006, and the flexural modulus, bending strain, and bending strength were measured. The results thus obtained are presented in the following Table 5.

TABLE 5

| | Flexural modulus (MPa) | Bending strain (%) | Bending strength (MPa) |
|---|---|---|---|
| Cured product 9 | 4750 | 2.6 | 132 |
| Cured product 10 | 5278 | 3.3 | 152 |
| Cured product 11 | 5007 | 3.0 | 138 |
| Cured product 12 | Not measurable | Not measurable | Not measurable |
| Cured product 13 | Not measurable | Not measurable | Not measurable |
| Cured product 14 | Not measurable | Not measurable | Not measurable |
| Cured product 15 | 4012 | 0.7 | 36 |
| Cured product 16 | Not measurable | Not measurable | Not measurable |

<Filler-Containing Composition>

Compositions including a maleimide compound and spherical silica as a filler were produced.

For the cured products thus obtained, fluidity was evaluated.

(Production of Composition)

Components were mixed according to the following Table 6, and the mixtures were melt-kneaded for 5 minutes at a temperature of 150° C. using two rolls. Thus, compositions 17 to 24 were produced. At this time, FB-560 (manufactured by Denka Company Limited) was used as spherical silica, KBM-403 (γ-glycidoxytriethoxysilane, manufactured by Shin-Etsu Chemical Co., Ltd.) as a silane coupling agent, and PEARL WAX No. 1-P (manufactured by CERARICA NODA Co., Ltd.) as carnauba wax.

TABLE 6

| | Maleimide compound | | Other resin | | Spherical silica | Silane coupling agent | Carnauba wax | Carbon black |
|---|---|---|---|---|---|---|---|---|
| | Type | Amount of incorporation (g) | Type* | Amount of incorporation (g) | Amount of incorporation (g) | Amount of incorporation (g) | Amount of incorporation (g) | Amount of incorporation (g) |
| Composition 17 | Example 3 | 131 | | | 860 | 2 | 1 | 3 |
| Composition 18 | Example 4 | 131 | | | 860 | 2 | 1 | 3 |
| Composition 19 | Example 5 | 131 | | | 860 | 2 | 1 | 3 |
| Composition 20 | Comparative Example 1 | 131 | | | 860 | 2 | 1 | 3 |
| Composition 21 | Comparative Example 2 | 131 | | | 860 | 2 | 1 | 3 |
| Composition 22 | Comparative Example 1 | 72 | BPA-DA | 59 | 860 | 2 | 1 | 3 |
| Composition 23 | Comparative Example 2 | 77 | BPA-DA | 24 | 860 | 2 | 1 | 3 |
| Composition 24 | Comparative Example 3 | 71 | BPA-DA | 60 | 860 | 2 | 1 | 3 |

*The details of the product name are as follows.
BPA-DA: Bisphenol A diallyl ether (manufactured by Gun Ei Chemical Industry Co., Ltd.)

(Fluidity)

A composition was injected into a test mold, and the spiral flow value was measured under the conditions of 175° C., 70 kg/cm$^2$, and 120 seconds. At this time, compositions 20 to 22 and 24 did not melt at 175° C., and measurement of the spiral flow value could not be carried out. The results thus obtained are presented in the following Table 7.

TABLE 7

|  | Spiral flow value (cm) |
|---|---|
| Composition 17 | 32 |
| Composition 18 | 58 |
| Composition 19 | 42 |
| Composition 20 | Not measurable |
| Composition 21 | Not measurable |
| Composition 22 | Not measurable |
| Composition 23 | 38 |
| Composition 24 | Not measurable |

<Dispersing Medium-Containing Composition and Laminate Including Cured Product of Composition>

Compositions including a maleimide compound and methyl ethyl ketone as an organic solvent were produced.

For the laminates thus obtained, the dielectric constant, dielectric loss tangent, and moisture-resistant solder resistance were evaluated.

(Production of Composition and Laminate Including Cured Product)

Compositions 25 to 32 were produced by mixing components according to the following Table 8. At this time, the non-volatile fraction (N.V.) of the compositions thus obtainable was 58% by mass.

Furthermore, the compositions 25 to 32 thus obtained were cured under the following conditions, and laminates 25 to 32 having a base material and a layer containing a cured product were produced.

However, in regard to the compositions 28 to 32, since the compositions were poorly soluble in methyl ethyl ketone, and cured products could not be produced, the evaluation of the dielectric constant, dielectric loss tangent, and moisture-resistant solder resistance could not be carried out.

Base material: Glass cloth for printed wiring board, "2116" (thickness: 100 μm, manufactured by NITTO BOSEKI CO., LTD.)

Number of plies: 6

Copper foil: TCR foil (thickness: 18 μm, manufactured by JX Nippon Mining & Metals Corporation)

Prepreg production conditions: 160° C./2 minutes Curing conditions: 200° C., 2.9 MPa, 2 hours Plate thickness after molding: 0.8 mm, amount of resin 40%

TABLE 8

| | Maleimide compound | | Other resin | | Methyl ethyl ketone |
|---|---|---|---|---|---|
| | Type | Amount of incorporation (g) | Type* | Amount of incorporation (g) | Amount of incorporation (g) |
| Composition 25 | Example 3 | 116 | | | 84 |
| Composition 26 | Example 4 | 116 | | | 84 |
| Composition 27 | Example 5 | 116 | | | 84 |
| Composition 28 | Comparative Example 1 | 116 | | | 84 |
| Composition 29 | Comparative Example 2 | 116 | | | 84 |

TABLE 8-continued

| | Maleimide compound | | Other resin | | Methyl ethyl ketone |
|---|---|---|---|---|---|
| | Type | Amount of incorporation (g) | Type* | Amount of incorporation (g) | Amount of incorporation (g) |
| Composition 30 | Comparative Example 1 | 64 | BPA-DA | 52 | 84 |
| Composition 31 | Comparative Example 2 | 68 | BPA-DA | 48 | 84 |
| Composition 32 | Comparative Example 3 | 63 | BPA-DA | 53 | 84 |

*The details of the product name are as follows.
BPA-DA: Bisphenol A diallyl ether (manufactured by Gun Ei Chemical Industry Co., Ltd.)

(Dielectric Constant and Dielectric Loss Tangent)

According to JIS C 6481:1999, the dielectric constant and dielectric loss tangent at 1 GHz of a laminate obtained after the laminate had been bone-dried and stored indoors at 23° C. and a humidity of 50% for 24 hours were measured using an impedance material analyzer "HP4291B" (manufactured by Agilent Technologies, Inc.). The results thus obtained are presented in the following Table 9.

(Moisture-Resistant Solder Resistance)

A laminate was left to stand for 168 hours in an atmosphere at 85° C. and 85% RH, and the laminate was subjected to a moisture absorption treatment. Next, the laminate that had been subjected to a moisture absorption treatment was immersed in a solder bath at 260° C. for 10 seconds, and the presence or absence of the generation of cracks was visually inspected. Incidentally, evaluation was carried out according to the following criteria. The results thus obtained are presented in the following Table 9.

◯: No generation of cracks
X: Cracks generated

TABLE 9

| | Dielectric constant | Dielectric loss tangent | Moisture-resistant solder resistance |
|---|---|---|---|
| Laminate 25 | 3.3 | 0.015 | ◯ |
| Laminate 26 | 3.0 | 0.011 | ◯ |
| Laminate 27 | 3.1 | 0.013 | ◯ |
| Laminate 28 | Not measurable | Not measurable | Not measurable |
| Laminate 29 | Not measurable | Not measurable | Not measurable |
| Laminate 30 | Not measurable | Not measurable | Not measurable |
| Laminate 31 | Not measurable | Not measurable | Not measurable |
| Laminate 32 | Not measurable | Not measurable | Not measurable |

<Photopolymerization Initiator-Containing Composition and Cured Product Thereof>

Compositions including a maleimide compound and a photopolymerization initiator were produced.

For the compositions thus obtained, curability was evaluated.

(Production of Composition)

Compositions 33 to 40 were produced by mixing components according to the following Table 10. At this time, IRGACURE 907 (2-methyl-1-[4-(methylthio)phenyl]-2-morpholino-1-propanone, manufactured by BASF SE) was used as a photopolymerization initiator.

However, compositions 36 to 40 had poor compatibility with photopolymerization initiator M-309 (trimethylolpropane triacrylate (TMPTA), manufactured by TOAGOSEI CO., LTD.), and the compositions could not be produced. Therefore, curability could not be evaluated.

TABLE 10

| | Maleimide compound | | Other resin | | Curing accelerator | | Photopolymerization initiator |
| --- | --- | --- | --- | --- | --- | --- | --- |
| | Type | Amount of incorporation (g) | Type* | Amount of incorporation (g) | Type* | Amount of incorporation (g) | Amount of incorporation (g) |
| Composition 33 | Example 3 | 50 | | | M-309 | 50 | 1 |
| Composition 34 | Example 4 | 50 | | | M-309 | 50 | 1 |
| Composition 35 | Example 5 | 50 | | | M-309 | 50 | 1 |
| Composition 36 | Comparative Example 1 | 50 | | | M-309 | 50 | 1 |
| Composition 37 | Comparative Example 2 | 50 | | | M-309 | 50 | 1 |
| Composition 38 | Comparative Example 1 | 28 | BPA-DA | 22 | M-309 | 50 | 1 |
| Composition 39 | Comparative Example 2 | 29 | BPA-DA | 21 | M-309 | 50 | 1 |
| Composition 40 | Comparative Example 3 | 27 | BPA-DA | 23 | M-309 | 580 | 1 |

*The details of the product name are as follows.
BPA-DA: Bisphenol A diallyl ether (manufactured by Gun Ei Chemical Industry Co., Ltd.)
M-309: Trimethylolprohane triacrylate (TMPTA, manufactured by TOAGOSEI CO., LTD.)

(Curability)
A composition was applied on a glass substrate to a thickness of 50 μm. Next, the composition was irradiated with ultraviolet radiation at a dose starting from 50 mJ/cm² at an increment of 10 mJ/cm², and the cumulative amount of light until the coating film surface became tack-free was measured. The results thus obtained are presented in Table 11.

TABLE 11

| | Cumulative amount of light (mJ/cm²) |
| --- | --- |
| Composition 33 | 120 |
| Composition 34 | 90 |
| Composition 35 | 130 |
| Composition 36 | Not measurable |
| Composition 37 | Not measurable |
| Composition 38 | Not measurable |
| Composition 39 | Not measurable |
| Composition 40 | Not measurable |

<Dispersing Medium-Containing Composition>
Compositions including a maleimide compound and methyl ethyl ketone as an organic solvent were produced.
For the compositions thus obtained, film-forming properties were evaluated.
(Production of Composition)
Compositions 41 to 48 were produced by mixing components according to the following Table 12. At this time, the non-volatile fraction (N.V.) of the compositions thus obtainable was 40% by mass.
However, since compositions 44 to 48 had poor solubility in methyl ethyl ketone, and compositions could not be produced, the film-forming properties could not be evaluated.

TABLE 12

| | Maleimide compound | | Other resin | | Methyl ethyl ketone |
| --- | --- | --- | --- | --- | --- |
| | Type | Amount of incorporation (g) | Type* | Amount of incorporation (g) | Amount of incorporation (g) |
| Composition 41 | Example 3 | 40 | | | 60 |
| Composition 42 | Example 4 | 40 | | | 60 |
| Composition 43 | Example 5 | 40 | | | 60 |
| Composition 44 | Comparative Example 1 | 40 | | | 60 |
| Composition 45 | Comparative Example 2 | 40 | | | 60 |
| Composition 46 | Comparative Example 1 | 22 | BPA-DA | 18 | 60 |
| Composition 47 | Comparative Example 2 | 23 | BPA-DA | 17 | 60 |
| Composition 48 | Comparative Example 3 | 22 | BPA-DA | 18 | 60 |

*The details of the product name are as follows.
BPA-DA: Bisphenol A diallyl ether (manufactured by Gun Ei Chemical Industry Co., Ltd.)

(Film-Forming Properties)
A composition was applied on a base material such that the thickness after curing would be 20 μm, and the composition was cured for 2 hours at 250° C. The external appearance was visually observed and evaluated according to the following criteria. The results thus obtained are presented in the following Table 13. Incidentally, regarding the base material, a standard stainless steel plate (SUS-304) was used.
○ . . . . A coating film is formed on the base material surface.
x . . . . Film formation does not occur.

TABLE 13

| | Film-forming properties |
| --- | --- |
| Composition 41 | ○ |
| Composition 42 | ○ |
| Composition 43 | ○ |
| Composition 44 | Not measurable |
| Composition 45 | Not measurable |
| Composition 46 | Not measurable |
| Composition 47 | Not measurable |
| Composition 48 | Not measurable |

INDUSTRIAL APPLICABILITY

The substituted or unsubstituted allyl group-containing maleimide compound of the invention is such that a cured product thereof undergoes low linear expansion and has excellent resistance to thermal decomposition. Therefore, the compound can be used suitably for a heat-resistant member or an electronic member. Particularly, the compound can be used suitably for a semiconductor encapsulating material, a circuit board, a buildup film, a buildup substrate, an adhesive, or a resist material. The compound can also be used suitably for a matrix resin of a fiber-reinforced resin, and is particularly suitable as a highly heat-resistant prepreg. Furthermore, since the compound exhibits photocurability, the compound can be suitably for various photocurable molding materials, and since compound exhibits film-forming properties, the compound can be suitably used as a resin for a heat-resistant coating material.

The invention claimed is:

1. A substituted or unsubstituted allyl group-containing maleimide compound, the compound having a structure with three or more benzene rings, having one or more groups each having a substituted or unsubstituted allyl group, and having one or more maleimide group,
wherein the structure with three or more benzene rings has at least one of structures represented by the following Formulae (1-1) to (1-11):

[Chem. 1]

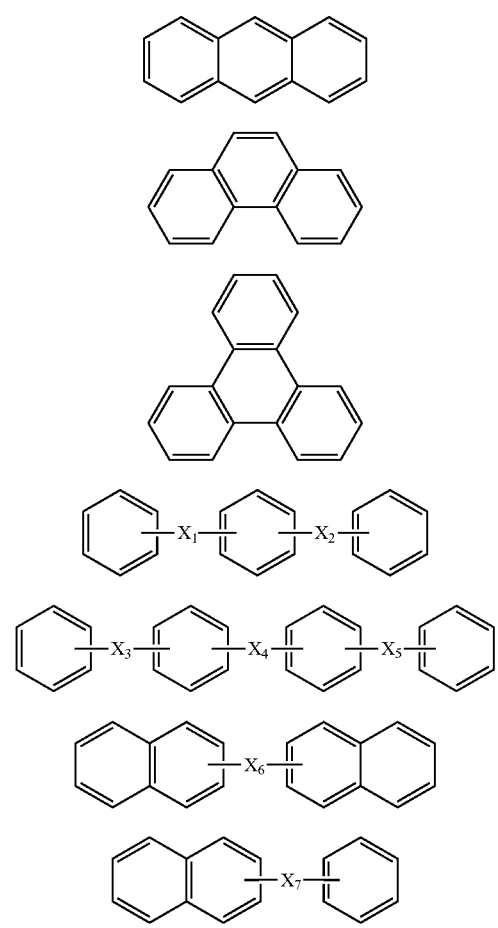

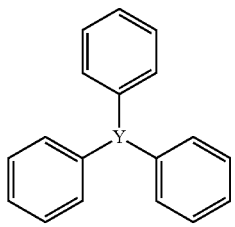

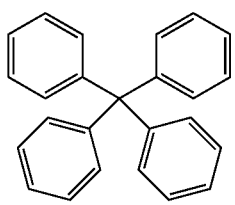

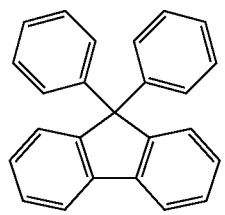

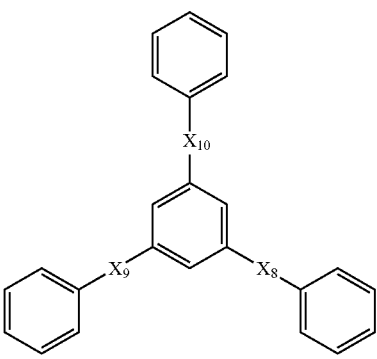

wherein
each benzene ring may have a substituent;
$X_1$ to $X_{10}$ each independently represent a direct bond, a hydrocarbon group having 1 to 3 carbon atoms which may have a substituent, an oxygen atom, a sulfur atom, or a sulfonyl group; and
Y represents a carbon atom which may have a substituent, or a nitrogen atom.

2. The substituted or unsubstituted allyl group-containing maleimide compound according to claim 1, wherein the compound is represented by the following Formula (2):

[Chem. 2]

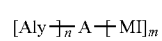

wherein
n and m each independently represent an integer from 1 to 5;
Aly represents a group containing a substituted or unsubstituted allyl group represented by the following Formula (3):

[Chem. 3]

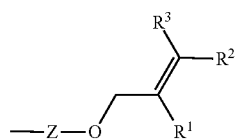

(3)

wherein Z represents a direct bond or a hydrocarbon group having 1 to 10 carbon atoms which may have a substituent; and $R^1$, $R^2$, and $R^3$ each independently represent a hydrogen atom or a methyl group;

MI represents a maleimide group represented by the following Formula (4):

[Chem. 4]

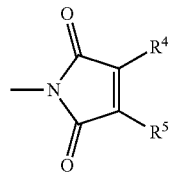

(4)

wherein $R^4$ and $R^5$ each independently represent a hydrogen atom or a methyl group; and A represents a structure having three or more benzene rings.

3. A composition comprising the substituted or unsubstituted allyl group-containing maleimide compound according to claim 1.

4. The composition according to claim 3, further comprising a reactive compound.

5. The composition according to claim 4, wherein the reactive compound is a compound having at least one selected from an epoxy group, a cyanate group, a maleimide group, a phenolic hydroxyl group, an oxazine ring, an amino group, and a group having a carbon-carbon double bond.

6. The composition according to claim 3, further comprising a filler.

7. The composition according to claim 3, further comprising a fibrous substrate.

8. A prepreg, comprising the composition according to claim 7.

9. A circuit board, comprising the prepreg according to claim 8 and a copper foil layer.

10. A cured product comprising a product formed by curing the composition according to claim 3.

11. A laminate, comprising a base material and a layer of the cured product according to claim 10.

12. The laminate according to claim 11, the laminate being a buildup film.

13. A buildup substrate, comprising the buildup film according to claim 12.

14. A heat-resistant member, comprising the cured product according to claim 10.

15. A composition for an electronic material, the composition comprising the composition according to claim 3.

16. A composition for a heat-resistant material, the composition comprising the composition according to claim 3.

17. An electronic member, comprising the cured product according to claim 10.

18. A semiconductor encapsulating material, comprising the composition according to claim 3.

19. A method for producing a substituted or unsubstituted allyl group-containing maleimide compound, the compound being a compound having a structure with three or more benzene rings, having one or more groups each having a substituted or unsubstituted allyl group, and having one or more maleimide groups, the method comprising:

1-1) a step of protecting an amino group of a hydroxyl group-containing aromatic amino compound having three or more benzene rings;

1-2) a step of introducing a substituted or unsubstituted allyl group into a hydroxyl group of the compound obtained in step 1-1);

1-3) a step of deprotecting the protected amino group of the compound obtained in step 1-2);

and 1-4) a step of maleimidating the amino group of the compound obtained in step 1-3).

* * * * *